United States Patent
Parker et al.

(10) Patent No.: US 11,828,759 B2
(45) Date of Patent: Nov. 28, 2023

(54) METHOD OF DIAGNOSIS

(71) Applicant: Peter MacCallum Cancer Institute, Melbourne (AU)

(72) Inventors: Belinda Sheree Parker, Alphington (AU); Hendrika Martha Duivenvoorden, Yarram (AU)

(73) Assignee: Peter MacCallum Cancer Institute, Melbourne (AU)

( * ) Notice: Subject to any disclaimer, the term of this patent is extended or adjusted under 35 U.S.C. 154(b) by 0 days.

(21) Appl. No.: 16/077,025

(22) PCT Filed: Feb. 10, 2017

(86) PCT No.: PCT/AU2017/050111
§ 371 (c)(1),
(2) Date: Aug. 9, 2018

(87) PCT Pub. No.: WO2017/136892
PCT Pub. Date: Aug. 17, 2017

(65) Prior Publication Data
US 2019/0033314 A1 Jan. 31, 2019

(30) Foreign Application Priority Data
Feb. 11, 2016 (AU) .............................. 2016900472

(51) Int. Cl.
| G01N 31/00 | (2006.01) |
|---|---|
| G01N 33/53 | (2006.01) |
| G01N 33/574 | (2006.01) |
| C12Q 1/6886 | (2018.01) |
| C12Q 1/68 | (2018.01) |
| A61K 39/00 | (2006.01) |
| A61N 5/00 | (2006.01) |

(52) U.S. Cl.
CPC .... *G01N 33/57415* (2013.01); *A61K 39/0011* (2013.01); *A61N 5/00* (2013.01); *C12Q 1/68* (2013.01); *C12Q 1/6886* (2013.01); *C12Q 2600/118* (2013.01); *C12Q 2600/158* (2013.01); *G01N 2333/8139* (2013.01)

(58) Field of Classification Search
None
See application file for complete search history.

(56) References Cited

U.S. PATENT DOCUMENTS

| 4,683,195 A | 7/1987 | Mullis et al. |
|---|---|---|
| 5,227,487 A | 7/1993 | Haugland et al. |
| 5,274,113 A | 12/1993 | Kang et al. |
| 5,326,692 A | 7/1994 | Brinkley et al. |
| 5,405,975 A | 4/1995 | Kuhn et al. |
| 5,433,896 A | 7/1995 | Kang et al. |
| 5,442,045 A | 8/1995 | Haugland et al. |
| 5,451,663 A | 9/1995 | Kang et al. |
| 5,453,517 A | 9/1995 | Kuhn et al. |
| 5,459,276 A | 10/1995 | Kuhn et al. |
| 5,516,864 A | 5/1996 | Kuhn et al. |
| 5,573,909 A | 11/1996 | Singer et al. |
| 5,648,270 A | 7/1997 | Kuhn et al. |
| 5,723,218 A | 3/1998 | Haugland et al. |
| 6,410,229 B1 | 6/2002 | Lockhart et al. |

FOREIGN PATENT DOCUMENTS

WO    WO 93/06121    4/1993

OTHER PUBLICATIONS

Zajc, I. etal., Cancer Letters. 2002, vol. 187, pp. 185-190 (Year: 2002).*
Coleman et al. (Frontiers in Bioscience 14, pp. 453-462, Jan. 1, 2009) (Year: 2009).*
Lah, T. etal., Human Pathology. 2000, vol. 31,No. 2, pp. 149-160 (Year: 2000).*
Nomura et al. (J. Med. Invest. vol. 52, pp. 1-9, Feb. 2005). (Year: 2005).*
Lee. S. et al. (Cancer Research. 2012. vol. 72. No. 17. pp. 4574-4586) (Year: 2012).*
Lee, S. et al., Cancer Research. 2011, vol. 71, supp. 18, Abstract A55 (Year: 2011).*
Zajc et al., Cancer Letters. 2002, vol. 187, pp. 185-190 (Year: 2002).*
Kuopio etal. (Cancer Research 58, 432-436. Feb. 1998) (Year: 1998).*
Adriance et al., Myoepithelial Cells: good fences make good neighbors. Breast Cancer Res. (2005) 7(5):190-197.
Alon et al., Broad patterns of gene expression revealed by clustering analysis of tumor and normal colon tissues probed by oligonucleotide arrays. PNAS U.S.A. (1999) 96:6745-6750.
Barsky et al., Myoepithelial Cells: Autocrine and Paracrine Suppressors of Breast Cancer Progression. J Mamm Gland Biol Neoplasia (2005) 10(3):249-260.

(Continued)

*Primary Examiner* — Lisa V Cook
(74) *Attorney, Agent, or Firm* — Knobbe, Martens, Olson & Bear, LLP

(57) ABSTRACT

The present invention relates generally to a method of detecting a risk of the progression from a pre-invasive neoplasia of the glandular epithelium. More particularly, the present invention provides a method of detecting a risk of the progression from a pre-invasive breast neoplasia by screening for the level of expression of Stefin A in the myoepithelial cells. The method of the present invention is useful in a range of applications including, but not limited to, assessing a neoplastic condition, monitoring the progression of such a condition, predicting the likelihood of a subject progressing to a more advance disease state or informing decisions in relation to the design of treatment schedules.

14 Claims, 16 Drawing Sheets

(56) References Cited

OTHER PUBLICATIONS

Blum et al., Noninvasive optical imaging of cysteine protease activity using fluorescently quenched activity-based probes. Nat Chem Biol. (2007) 3(10):668-677.

Bidwell et al., Silencing of Irf7 pathways in breast cancer cells promotes bone metastasis through immune escape. Nat Med. (2012) 18(8):1224-1231.

Brosch et al., Accurate and Sensitive Peptide Identification with Mascot Percolator. J Proteome Res. (2009) 8(6):3176-3181.

Chang et al., Identification of candidate nasopharyngeal carcinoma serum biomarkers by cancer cell secretome and tissue transcriptome analysis: Potential usage of cystatin A for predicting nodal stage and poor prognosis. Proteomics (2010) 10:2644-2660.

DeRisi et al., Use of a cDNA microarray to analyse gene expression patterns in human cancer. Nat Genet. (1996) 14(4):457-460.

Dubin G., Proteinaceous cysteine protease inhibitors. Cell Mol Life Sci. (2005) 62:653-669.

Erlich H.A., Polymerase Chain Reaction. J Clin Immunol. (1989) 9(6):437-447.

Fujiki et al., Isolation of Intracellular Membranes by Means of Sodium Carbonate Treatment: Application to Endoplasmic Reticulum. J Cell Biol. (1982) 93(1):97-102.

Germer et al., High-Throughput SNP Allele-Frequency Determination in Pooled DNA Samples by Kinetic PCR. Genome Res. (2000) 10(2):258-266.

Gocheva et al. Distinct roles for cysteine cathepsin genes in multistage tumorigenesis. Genes Dev. (2006) 20(5):543-556.

Gopal et al., YBX1/YB-1 induces partial EMT and tumourigenicity through secretion of angiogenic factors into the extracellular microenvironment. Oncotarget. (2015) 6(15):13718-13730.

Greening et al., Colon tumour secretopeptidome: Insights into endogenous proteolytic cleavage events in the colon tumour microenvironment. Biochim Biophys Acta. (2013) 1834:2396-2407.

Greening et al., Human Endometrial Exosomes Contain Hormone-Specific Cargo Modulating Trophoblast Adhesive Capacity: Insights into Endometrial-Embryo Interactions. Biol Reprod. (2016) 94(2):38 in 15 pages.

Gudjonsson et al., Normal and tumor-derived myoepithelial cells differ in their ability to interact with luminal breast epithelial cells for polarity and basement membrane deposition. J Cell Sci. (2002) 115(Pt 1):39-50.

Guo et al., Direct fluorescence analysis of genetic polymorphisms by hybridization with oligonucleotide arrays on glass supports. Nucl Acids Res. (1994) 22(24):5456-5465.

Heid et al., Real Time Quantitative PCR. Genome Res. (1996) 6(10):986-994.

Hu et al., Regulation of In Situ to Invasive Breast Carcinoma Transition. Cancer Cell. (2008) 13:394-406.

Keppler D., Towards novel anti-cancer strategies based on cystatin function. Cancer Lttr. (2006) 235:159-176.

Kuopio et al., Cysteine Proteinase Inhibitor Cystatin A in Breast Cancer. Cancer Res. (1998) 58:432-436.

Lah et al., Cells Producing Cathepsins D, B, and L in Human Breast Carcinoma and Their Association With Prognosis. Human Pathology (2000) 31(2):149-160.

Lee et al., Abstract A55: Genes regulating the progression of human ductal carcinoma in situ to invasive breast cancer. Cancer Genomics—$2^{nd}$ AACR Conference on Frontiers in Basic Cancer Research; Sep. 14-18, 2011 in 2 pages.

Lee et al., Differentially Expressed Genes Regulating the Progression of Ductal Carcinoma In Situ to Invasive Breast Cancer. Cancer Res. (2012) 72(17):4574-4586.

Maskos et al., Oligonucleotide hybridisations on glass supports: a novel linker for oligonucleotide synthesis and hybridization properties of oligonucleotides synthesised in situ, Nucl Acids Res. (1992) 20(7):1679-1684.

Miller et al., MCF10DCIS.com Xenograft Model of Human Comedo Ductal Carcinoma In Situ, J Nat Cancer Institute (2000) 92(14):1185-1186.

Moore et al., Measuring transferrin receptor gene expression by NMR imaging, Biochim Biophys Acta (1998) 1402:239-249.

Mullins et al., Three-dimensional cultures modeling premalignant progression of human breast epithelial cells: role of cysteine cathepsins. Biol Chem. (2012) 393(12):1405-1416.

Mullis et al., Specific Synthesis of DNA in Vitro via a Polymerase-Catalyzed Chain Reaction. Methods Enzymol. (1987) 155:335-350.

Nesvizhshii et al., Interpretation of Shotgun Proteomic Data—The Protein Inference Problem. Mol Cell Proteomics (2005) 4(10):1419-1440.

Obermajer et al., Immunonanoparticles—an effective tool to impair harmful proteolysis in invasive breast tumor cells. FEBS (2007) 274(17):4416-4427.

Parker et al., Primary tumour expression of the cysteine cathepsin inhibitor Stefin A inhibits distant metastasis in breast cancer. J Pathol. (2008) 214(3):337-346.

Pease et al., Light-generated oligonucleotide arrays for rapid DNA sequence analysis. PNAS U.S.A. (1994) 91:5022-5026.

Polyak et al., Do Myoepithelial Cells Hold the Key for Breast Tumor Progression? J Mamm Gland Biol Neoplasia (2006) 10(3):231-247.

Polyak K., Molecular Markers for the Diagnosis and Management of Ductal Carcinoma In Situ. J Natl Cancer Inst Monogr. (2010) 2010(41):210-213.

Runswick et al., Desmosomal adhesion regulates epithelial morphogenesis and cell positioning. Nat Cell Biol. (2001) 3:823-830.

Schena et al., Quantitative Monitoring of Gene Expression Patterns with a Complementary DNA Microarray. Science (1995) 270:467-470.

Schindelin et al., Fiji—an Open Source platform for biological image analysis. Nat Methods. (2012) 9(7):15 pages.

Schnitt S.J., The Transition from Ductal Carcinoma In Situ to Invasive Breast Cancer. Breast Cancer Res. (2009) 11(1):101 in 2 pages.

Sgroi D.C., Preinvasive Breast Cancer. Annu Rev Pathol. (2010) 5:193-221.

Smith et al., Direct Mechanical Measurements of the Elasticity of Single DNA Molecules by Using Magnetic Beads. Science (1992) 258:1122-1126.

Sternlicht et al., The myoepithelial defense: a host defense against cancer. Med Hypotheses (1997) 48:37-46.

Sternlicht et al., The human myoepithelial cell is a natural tumor suppressor. Clin Cancer Res. (1997) 3:1949-1958.

Strojan et al., Cysteine proteinase inhibitor cystatin C in squamous cell carcinoma of the head and neck: relation to prognosis. Brit J Cancer (2004) 90:1961-1968.

Strojnik et al., Cathepsin B and its inhibitor stefin A in brain tumors. Eur J Physiol. (2000) 439(Suppl):R122-R123.

Tang et al., Expression and Prognostic Significance of Macrophage Inflammatory Protein-3 Alpha and Cystatin A in Nasopharyngeal Carcinoma. Biomed Res Int. (2015) 617143 in 6 pages.

Urdea et al., Branched DNA amplification multimers for the sensitive, direct detection of human hepatitis viruses. Nucleic Acids Symp Ser. (1991) 24:197-200 [Abstract Only].

Verdoes et al., An improved quenched fluorescent probe for imaging of cysteine cathepsin activity. J Am chem Soc. (2013) 135(39) in 10 pages.

Vichai et al., Sulforhodamine B colorimetric assay for cytotoxicity screening. Nat Protoc. (2006) 1(3):1112-1116.

Wedemeyer et al., Flow Cytometric Quantification of Competitive Reverse Transcription—PCR Products. Clin Chem. (2002) 48(9):1398-1405.

Weissleder et al., In vivo magnetic resonance imaging of transgene expression. Nature Med. (2000) 6(3):351-354.

Wood et al., The Current Clnical Value of the DCIS Score. Oncology (Williston Park) (2014) 28(suppl 2): in 10 pages.

Zajc et al., Expression of cysteine peptidase cathepsin L and its inhibitors stefins A and B in relation to tumorigenicity of breast cancer cell lines. Cancer Ltt (2002) 187:185-190.

(56) References Cited

OTHER PUBLICATIONS

Zardawi et al., High Notch1 protein expression is an early event in breast cancer development and is associated with the HER-2 molecular subtype. Histopathol. (2010) 56:286-296.
International Search Report and Written Opinion dated May 1, 2017 in corresponding International Application PCT/AU2017/050111 in 11 pages.
Alon et al., Broad patterns of gene expression revealed by clustering analysis of tumor and normal colon tissues probed by oligonucleotide arrays, Proc. Natl. Acad. Sci. USA, vol. 96, pp. 6745-6750, Jun. 1999 Cell Biology.
Barsky et al., Myoepithelial Cells: Autocrine and Paracrine Suppressors of Breast Cancer Progression, Journal of Mammary Gland Biology and Neoplasta, vol. 10, No. 3, Jul. 2005. Doi:10.1007/s10911-005-9585-5.
Blum et al., Noninvasive optical imaging of cysteine protease activity using fluorescently quenched activity-based probes, Nature chemical biology, vol. 3, No. 10, pp. 668-677, Oct. 2007.
Brosch et al., Accurate and Sensitive Peptide Identification with Mascot Percolator, J Proteome Res. Jun. 2009; doi:10.1021/pr800982s.
Chang et al., Identification of candidate nasopharyngeal carcinoma serum biomarkers by cancer cell secretome and tissue transcriptome analysis: Potential usage of cystatin A for predicting nodal stage and poor prognosis, Proteomics, Oct. 2010, 2644-2660, doi: 10.1002/pmic200900620.
DeRisi et al., Nature Genetics (1996) 14:457-460.
Lee et al., Differentially Expressed Genes Regulating the Progression of Ductal Carcinoma In Situ to Invasive Breast Cancer, Cancer Res. Sep. 2012, 72 (17), 4574-4586, doi: 10.1158/0008-5472.CAN-12-0636.
Lee et al., Abstract A55: Genes regulating the progression of human ductal carcinoma in situ to invasive breast cancer, Doi: 10.1158/1538-7445. FBCR11-A55, Sep. 2011.
Dubin, Proteinaceous cysteine protease inhibitors, CMLS Cellular and Molecular Life Sciences, 62 (2005) 653-669, doi: 10.1007/s00018-004-4445-9.
Erlich, Polymerase Chain Reaction, Journal of Clinical Immunology, vol. 9, No. 6, 1989.
Fujiki et al., Isolation of Intracellular Membranes by Means of Sodium Carbonate Treatment: Application to Endoplasmic Reticulum, The Journal of Cell Biology, vol. 93, Apr. 1982, 97-102.
Germer et al., Genome Res. (2000) 10:258-266.
Gocheva et al., Distinct roles for cysteine cathepsin genes in multistage tumorigenesis, Genes & Development, 2006, 543-556.
Gopal et al., YBX1/YB-1 induces partial EMT and tumourgenicity through secretion of angiogenic factors into the extracellular microenvironment, Oncotarget, vol. 6, No. 15, 13718-13730.
Greening et al., Colon tumour secretopeptidome: Insights into endogenous proteolytic cleavage events in the colon tumour microenvironment, Biochimica et Biophysica Acta 1834 (2013) 2396-2407.
Greening et al., Human Endometrial Exosomes Contain Hormone-Specific Cargo Modulating Trophoblast Adhesive Capacity: Insights into Endometrial-Embryo Interactions, Biology of Reproduction, 2016, 94(2):38, 1-15.
Gudjonsson et al., Normal and tumor-derived myoepithelial cells differ in their ability to interact with luminal breast epithelial cells for polarity and basement membrane deposition, J Cell Sci. Jan. 2002, 115(Pt 1): 39-50.
Guo et al., Direct fluorescence analysis of genetic polymorphisms by hybridization with oligonucleotide arrays on glass supports, Nucleic Acids Research, 1994, vol. 22, No. 24, 5456-5465.
Heid et al., Genome Res. (1996) 6:986-994.
Huang et al., Systematic and integrative analysis of large gene lists using DAVID bioinformatics resources, Nature Protocols, 2009, vol. 4, No. 1, 44-57.
Kanehisa et al., KEGG: Kyoto Encyclopedia of Genes and Genomes, Nucleic Acids Research, 2000, vol. 28, No. 1, 27-30.

Keller et al., Empirical Statistical Model To Estimate the Accuracy of Peptide Identifications Made by MS/MS and Database Search, Anal. Chem. 2002, 74, 5383-5392.
Keppler, Towards novel anti-cancer strategies based on cystatin function, Cancer Letters, 235 (2006) 159-176.
Maskos and Southern, Nuc. Acids Res. (1992) 20: 1679-84.
Kuopio et al., Cysteine Proteinase Inhibitor Cystatin A in Breast Cancer, Cancer Research 58, 432-436, Feb. 1998.
Lah et al., Cells Producing Cathepsins D, B. and L in Human Breast Carcinoma and Their Association With Prognosis, Human Pathology, vol. 31, No. 2, Feb. 2000, 149-160.
Miller et al., Xenograft Model of Human Comedo Ductal Carcinoma In Situ, Journal of the National Cancer Institute, vol. 92, No. 14, Jul. 2000, 1185-1186.
Moore et al., BBA (1988), 1402:239-249.
Mullins et al., Three-dimensional cultures modeling premalignant progression of human breast epithelial cells: role of cysteine cathepsins, Biol Chem. Dec. 2012; 393(12): 1405-1416.
Mullis et al., Specific Synthesis of DNA in Vitro via a Polymerase-Catalyzed Chain Reaction, Methods in Enzymology, vol. 155, pp. 335-350.
Nesvizhskii et al., Interpretation of Shotgun Proteomic Data, Molecular & Cellular Proteomics 4.10, 2005, 1419-1440.
Parker BS et al., Journal of Pathology (2008) 213 (3):337-46.
Pease et al., Proc. Natl. Acad. Sci. (1994) USA 91(11): 5022-5026.
Polyak et al., Do Myoepithelial Cells Hold the Key for Breast Tumor Progression? Journal Mammary Gland Biology and Neoplasta, vol. 10, No. 3, Jul. 2005, 231-247.
Runswick et al., Desmosomal adhesion regulates epithelial morphogenesis and cell positioning, Nature Cell Biology, vol. 3, Sep. 2001, 823-830.
Schena et al., Science (1995) 270:467-470.
Schindelin et al., Fiji—an Open Source platform for biological image analysis, Nat Methods. 2012 ; 9(7): doi: 10.1038/nmeth2019.
Smith et al., Science (1992) 258:1122-1126.
Sternlicht et al., The myoepithelial defense: a host defense against cancer, Medical Hypotheses, (1997) 48, 37-46.
Sternlicht et al., The Human Myoepithelial Cell Is a Natural Tumor Suppressor, Clinical Cancer Research, vol. 3, Nov. 1997, 1949-1958.
Strojan et al., Cysteine proteinase inhibitor cystatin C in squamous cell carcinoma of the head and neck: relation to prognosis, British Journal of Cancer, (2004) 90, 1961-1968.
Strojnik et al., Cathepsin B and its inhibitor stefin A in brain tumors, Pflugers Arch—Eur J Physiol (2000) 439 [Suppl]: R122-R123.
Urdea et al., Nucleic Acids Symp. Ser., (1991) 24:197-200.
Tang et al., Expression and Prognostic Significance of Macrophage Inflammatory Protein-3 Alpha and Cystatin A in Nasopharyngeal Carcinoma, BioMed Research International, vol. 2015, Article ID 617143, 6 pages.
Tang et al., ggfortify: Unified Interface to Visualize Statistical Results of Popular R Packages, The R Journal, vol. 8/2, Dec. 2016, 474-485.
Verdoes et al., An improved quenched fluorescent probe for imaging of cysteine cathepsin activity, J Am Chem Soc. Oct. 2013; 135(39).
Vichai et al., Sulforhodamine B colorimetric assay for cytotoxicity screening, Nature Protocols, vol. 1, No. 3, 2006, 1112-1116.
Wedemeyer et al., Clinical Chemistry (2002) 48:1398-1405.
Weissleder et al., Nature Medicine (2000) 6:351-355.
Wickham, ggplot2: Elegant Graphics for Data Analysis, (2009) 1ed. New York: Springer-Verlag.
Wood et al., The Current Clinical Value of the DCIS Score, Cancer Network, May 2014, 10 pages.
Zajc et al., Expression of cysteine peptidase cathepsin L and its inhibitors stefins A and B in relation to tumorigenicity of breast cancer cell lines, Cancer Letters, 187 (2002) 185-190.
Zardawi et al., High Notch1 protein expression is an early event in breast cancer development and is associated with the HER-2 molecular subtype, Histopathology 2010, 56, 286-296.
Gudjonsson et al., Myoepithelial Cells: Their Origin and Function in Breast Morphogenesis and Neoplasia, J Mammary Gland Biol Neoplasia. Jul. 2005; 10(3): 261-272. Doi: 10.1007/s10911-005-9586-4.

(56) References Cited

OTHER PUBLICATIONS

Jones, et al., Expression Profiling of Purified Normal Human Liminal and Myoepithelial Breast Cells: Identification of Novel Prognostic Markers for Breast Cancer. Cancer Research 64, 3037-3045, May 1, 2004.

* cited by examiner

*citrate buffer only control

| Patient 1997 - Had recurrence | Patient 2004 - Had recurrence | Patient 2001 - No recurrence |
|---|---|---|
|  |  |  |

METHOD OF DIAGNOSIS

CROSS REFERENCE TO RELATED APPLICATIONS

This application is a U.S. National Phase Application of PCT International Application Number PCT/AU2017/050111, filed on Feb. 10, 2017, designating the United States of America and published in the English language, which is an International Application of and claims the benefit of priority to Australian Patent Application No. 2016900472, filed on Feb. 11, 2016. The disclosures of the above-referenced applications are hereby expressly incorporated by reference in their entireties.

FIELD OF THE INVENTION

The present invention relates generally to a method of detecting a risk of the progression from a pre-invasive neoplasia of the glandular epithelium. More particularly, the present invention provides a method of detecting a risk of the progression from a pre-invasive breast neoplasia by screening for the level of expression of Stefin A in the myoepithelial cells. The method of the present invention is useful in a range of applications including, but not limited to, assessing a neoplastic condition, monitoring the progression of such a condition, predicting the likelihood of a subject progressing to a more advance disease state or informing decisions in relation to the design of treatment schedules.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

A neoplasm is an abnormal mass or colony of cells produced by a relatively autonomous new growth of tissue. Most neoplasms arise from the clonal expansion of a single cell that has undergone neoplastic transformation. The transformation of a normal cell to a neoplastic cell can be caused by a chemical, physical, or biological agent (or event) that alters the cell genome. Neoplastic cells are characterized by the loss of some specialized functions and the acquisition of new biological properties, foremost the property of relatively autonomous growth. They pass on their heritable biological characteristics to progeny cells. Neoplasms may originate in almost any tissue containing cells capable of mitotic division.

The past, present, and future predicted biological behaviour, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm, however, exhibits a lesser degree of autonomy, is usually not invasive and does not metastasize.

Breast cancer will directly impact 1 in 8 women in Australia in their lifetime and is the second leading cause of cancer-related death in women. Due to mammographic screening, approximately 25% of breast cancers are diagnosed at an early stage that has not yet invaded the breast tissue, termed non-invasive cancers. Nevertheless, approximately 15% of breast cancer patients will develop spread (metastasis) to distant organs such as liver, brain, lung and bone.

Breast cancer usually begins either in the cells of the lobules, which are milk-producing glands, or the ducts, the passages that drain milk from the lobules to the nipple. Non-invasive cancers which are confined to the milk ducts or lobules in the breast are termed carcinoma in situ or pre-cancers. Invasive cancers, however, grow into the normal, healthy breast tissue, with metastatic spread beyond the breast being characteristic of highly aggressive, end stage disease.

In some cases a breast cancer may be both invasive and non-invasive, meaning that part of the cancer has grown into normal tissue while part of the cancer has remained inside the milk ducts or milk lobules. A breast cancer also may be characterised as a "mixed tumour", meaning that it contains a mixture of cancerous ductile cells and lobular cells. This type of cancer is also termed an "invasive mammary breast cancer" or an "infiltrating mammary carcinoma". It is usually treated as a ductile carcinoma.

If there is more than one tumour in the breast, the breast cancer is described as either multifocal or multicentric. In multifocal breast cancer, all of the tumours arise from the original tumour, and are usually in the same section of the breast, while if the cancer is multicentric, the tumours have formed separately, and are often found in different areas of the breast.

Generally, a breast cancer can be classified as one of the following:
  DCIS (Ductal carcinoma in situ): a non-invasive cancer which is contained within the milk duct.
  LCIS (Lobular carcinoma in situ): is an overgrowth of cells which is contained within the lobule.
  IDC (Invasive ductal carcinoma): the most common type of breast cancer. Invasive ductal carcinoma begins in the milk duct as a DCIS but grows into the surrounding normal tissue inside the breast.
  Less common subtypes of invasive ductal carcinoma can include tubular, medullary, mucinous, papillary, and cribriform carcinomas of the breast. In these cancers, the cells can look and behave somewhat differently than invasive ductal carcinoma cells usually do.
  ILC (Invasive lobular carcinoma): starts inside the lobule but grows into the surrounding normal tissue inside the breast.
  Inflammatory breast cancer: a fast-growing form of breast cancer that usually starts with the reddening and swelling of the breast, instead of a distinct lump.
  Male breast cancer: rare, but when it occurs, is almost always a ductal carcinoma.
  Padget's disease of the nipple: a rare form of breast cancer in which cancer cells collect in or around the nipple.
  Phyllodes tumours of the breast: rare breast tumours that begin in the connective tissue of the breast (stroma) and grow quickly in a leaflike pattern.
  Recurrent and/or metastatic breast cancer: Breast cancer that has returned after previous treatment or has spread beyond the breast to other parts of the body.

Of the cancers detected by mammographic screening which are early stage (approximately 25% of all patients), the majority of these correspond to ductal carcinoma in situ (DCIS). There are multiple pathological grades of DCIS, these being low, intermediate and high, with high-grade DCIS lesions more likely to progress to invasive carcinoma (IDC) than low-grade lesions. Progression of DCIS to IDC significantly increases the risk of tumour cell dissemination and subsequent metastasis. However it is currently not possible to accurately predict which patients will develop invasive cancer. Some DCIS, if untreated, will rapidly progress to invasive cancer, while others will change very little in 5-20 years. However, although DCIS represents a significant (up to 25%) fraction of newly diagnosed breast cancer cases, the clinical management of DCIS patients is still inconclusive.

In the absence of the ability to discriminate between DCIS with differing prognosis, current methods of treating these cancers continue to follow the long used protocol of surgical excision (if possible) followed by radiotherapy and/or chemotherapy These treatments are associated with severe side effects including disfigurement and scarring from surgery (e.g. mastectomy or limb amputation), severe nausea and vomiting from chemotherapy, and most significantly, damage to normal tissues such as the hair follicles, gut and bone marrow which is induced as a result of the relatively non-specific targeting mechanism of the toxic drugs which form part of most cancer treatments. To the extent that a proportion of DCIS are unlikely to progress, patients are unnecessarily subjected to these aggressive forms of treatment. To the extent that patients do develop a form of DCIS which is likely to progress, knowing this would inform both treatment and ongoing patient management, such as in the context of the risk of lymphodema and secondary cancers due to the use of DNA damaging agents such as radiotherapy and chemotherapy.

Accordingly, there is an urgent need to develop methods of discriminating between early stage DCIS which will not progress versus those which are likely either to progress to invasive disease or, even if treated, are likely to relapse/recur. Currently there is no means to reliably and routinely assess and/or monitor a patient in this way.

To date, research in relation to the diagnosis or prognosis of neoplasia has focused on the analysis of phenotypic or epigenetic changes to the neoplastic cell itself. However, in work leaking up to the present invention, it has been unexpectedly determined that a phenotypic change to the cells proximal to a neoplastic cell in a glandular tissue may provide an accurate prognostic marker. More specifically, a decrease in the level of Stefin A expression by myoepithelial cells has been determined to be indicative of both the increased likelihood of progression of the disease to an invasive state and the likely relapse of a patient. However, still more unexpectedly, it has been determined that patients who maintain normal Stefin A expression levels in the myoepithelial cells in fact need not undergo treatment at all, in particular radiotherapy.

This finding has the potential to revolutionise the treatment protocols for patients presenting with early stage/pre-invasive breast cancer since a large proportion of breast cancer patients with DCIS currently receive surgery and radiotherapy (some also chemotherapy), yet prospective studies show that less than 10% actually gain a survival benefit. Many breast cancer patients will not develop metastatic disease and do not require therapeutic intervention at all. Accordingly, the method of the present invention has, for the first time, provided a means of predicting which patients presenting with pre-invasive breast cancer can be spared treatment entirely. This information in relation to the expression of Stefin A can therefore inform the development of the therapeutic treatment and ongoing monitoring which is appropriate for a breast cancer patient.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

Accordingly, one aspect of the present invention is directed to a method of prognosing a risk of progression from a pre-invasive epithelial neoplasia associated with the glandular epithelium in a mammal, said method comprising screening for the level of expression of Stefin A in myoepithelial cells wherein a decrease in the level of Stefin A expression relative to a control level is indicative of an increased risk of progression of the neoplasia.

Another aspect of the present invention is directed to a method of prognosing a risk of progression from a pre-invasive breast neoplasia in a mammal, said method comprising screening for the level of expression of Stefin A in breast myoepithelial cells wherein a decrease in the level of Stefin A expression relative to a control level is indicative of an increased risk of progression of the neoplasia.

In another aspect there is provided a method of prognosing a risk of progression from a pre-invasive breast neoplasia in a mammal, said method comprising screening for the level of expression of Stefin A in breast myoepithelial cells wherein a decrease in the level of Stefin A expression relative to a normal level is indicative of an increased risk of progression of the neoplasia.

In still another there is provided a method of prognosing a risk of progression from a pre-invasive breast carcinoma in a mammal, said method comprising screening for the level of expression of Stefin A in breast myoepithelial cells wherein a decrease in the level of Stefin A expression relative to a control level is indicative of an increased risk of progression.

In a further aspect there is provided a method of prognosing a risk of progression from a pre-invasive breast lobular or ductal neoplasia in a mammal, said method comprising screening for the level of expression of Stefin A in breast myoepithelial cells wherein a decrease in the level of Stefin A expression relative to a control level is indicative of an increased risk of progression.

In still a further aspect there is provided a method of prognosing a risk of progression from a pre-invasive breast ductal neoplasia in a mammal, said method comprising screening for the level of expression of Stefin A in breast ductal myoephithelial cells wherein a decrease in the level of Stefin A expression relative to a control level is indicative of an increased risk of progression.

Preferably, said myoepithelial cells are localised to the same tissue region as the neoplasia and, in a particular embodiment, are located adjacent or proximal to the neoplasia.

In a related aspect, said neoplasia progression is the transition to an invasive phenotype.

In a further aspect, the present invention provides a method of prognosing a risk of progression from a pre-invasive breast neoplasm in a mammal, said method comprising screening for the level of expression of Stefin A in breast myoepithelial cells wherein a decrease in the level of Stefin A expression relative to a normal level is indicative of an increased risk of progression.

In yet another further aspect there is provided a method of monitoring a patient for a risk of progression from a pre-invasive breast neoplasia in an mammal, said method comprising screening for the level of expression of Stefin A in breast myoepithelial cells wherein a decrease in the level of Stefin A expression relative to a previous test result level is indicative of an increased risk of progression of the neoplasia.

In still a further aspect there is provided a method of informing treatment regimes or determining whether to treat a mammal presenting with a pre-invasive breast neoplasia, said method comprising screening for the level of expression of Stefin A in breast myoepithelial cells wherein:
  (i) a decrease in the level of Stefin A expression relative to a normal level is indicative of an increased risk of progression and the need for treatment; or
  (ii) no change in relation to the level of Stefin A expression relative to a normal level is indicative of a low risk of progression and no need for treatment.
  Preferably, said treatment regimes includes:
  a) Cysteine cathepsin inhibitors;
  b) Surgical excision;
  c) Radiotherapy;
  d) Chemotherapy;
  e) Targeted antibody therapy; and/or
  f) Endocrine therapy In yet still a further aspect there is provided a method of determining whether to treat a mammal being monitored for the progression from a pre-invasive breast neoplasia, said method comprising screening for the level of expression of Stefin A in breast myoepithelial cells wherein a decrease in the level of Stefin A expression relative to a previous test result level is indicative of an increased risk of progression and the need for treatment.

In a further aspect there is provided a method for detecting micro-invasive lesions in breast neoplasia associated with the glandular epithelium in a mammal, said method comprising screening for the level of Stefin A in myoepithelial cells wherein a decrease in the level of Stefin A expression relative to a control and/or normal level is indicative of an increased risk of micro-invasion of the neoplasia.

In a related aspect there is provided a method for prognosing, monitoring a risk of progression, informing treatment regimes, determining whether to treat and/or determining whether to treat a mammal for the progression from a pre-invasive breast neoplasia, said method comprising screening for the level of expression of Stefin A in breast myoepithelial cells wherein a decrease in the level of Stefin A expression and further screening a change in expression of one or more membrane adhesion molecules relative to a control and/or normal level, wherein said membrane adhesion molecules include:
  a) DSG3; and/or
  b) MINK1, ASAP2, ZNF185, TJP2, SVIL, MYH10, LAMC1, TANC1, ILKAP, FAM129B, PALLD, PTRF, PDLIM5, TNS4, GAK, LANCL1, MYH9, THBS1, LRRC16A, FER, SYNE2, SYNE1, ENAH, PKP2, SNTB2, PARVA, PRKD2, KDF1, COL7A1, CSK, ARPC2, SNAP23, JUP, ARF1, NPTN, MTDH, ACTN1, CFL1, LAMA3, DSC3, STOML2, FSCN1, AP2A1, ACTN4, NDRG1, LAMC2, LIMA1, FERMT1, PI4K2A, OCLN, KRT1, RAP1A, FAP, ARFGEF2, FAM120A, CD44, CIB1, COL12A1, DST, ATP1B1, ATAD1, LAMB1, CDH4, FAT2, PVR, CD109, CDH13, PKP4, CD63, PCDH1, GJA1, MPST, PSEN1, CLCA2, MELTF, SLC7A5, FOCAD, MISP, VEZT, EPHB4, RUSC1, RAB13 is indicative of an increased risk of progression.

In another aspect there is provided a method for further screening for other variables including estrogen receptor, progesterone receptor and/or human epidermal growth factor receptor 2 (HER2).

In a further aspect there is provided a method of prognosis and/or monitoring a patient risk of progression from a pre-invasive breast neoplasia in a mammal, said method comprising assessing the level of expression of Stefin A and one or more markers in myoepithelial cells wherein the one or more other markers include:
  a. Cysteine cathepsin protease; and/or
  b. one or more of the following membrane adhesion molecules
    i. DSG3; and/or
    ii. MINK1, ASAP2, ZNF185, TJP2, SVIL, MYH10, LAMC1, TANC1, ILKAP, FAM129B, PALLD, PTRF, PDLIM5, TNS4, GAK, LANCL1, MYH9, THBS1, LRRC16A, FER, SYNE2, SYNE1, ENAH, PKP2, SNTB2, PARVA, PRKD2, KDF1, COL7A1, CSK, ARPC2, SNAP23, JUP, ARF1, NPTN, MTDH, ACTN1, CFL1, LAMA3, DSC3, STOML2, FSCN1, AP2A1, ACTN4, NDRG1, LAMC2, LIMA1, FERMT1, PI4K2A, OCLN, KRT1, RAP1A, FAP, ARFGEF2, FAM120A, CD44, CIB1, COL12A1, DST, ATP1B1, ATAD1, LAMB1, CDH4, FAT2, PVR, CD109, CDH13, PKP4, CD63, PCDH1, GJA1, MPST, PSEN1, CLCA2, MELTF, SLC7A5, FOCAD, MISP, VEZT, EPHB4, RUSC1, RAB13.

In a further aspect there is provided a method of assessing a risk of relapse of an neoplasia associated with the glandular epithelium in a mammal, said method comprising screening for the level of expression of Stefin A in myoepithelial cells wherein a decrease in the level of Stefin A expression relative to a control level is indicative of an increased risk of relapse of the neoplasia or relapse.

Preferably, the mammal is a human

In still a further aspect of the invention, there is provided a kit for assaying biological samples said kit comprising
  a. an agent for detecting Stefin A;
  b. reagent for detecting said agent; and
  c. a control
  when used for detecting a pre-invasive epithelial neoplasia or assessing the risk of progression and/or diagnosing/monitoring progression or relapse of an neoplasia associated with the glandular epithelium in a mammal wherein a decrease in the level of Stefin A expression relative to a control level is indicative of an increased risk of progression of the neoplasia or relapse of the neoplasia or relapse.

In a related aspect, the kit may further comprise
  a. cysteine cathepsin protease; and/or
  b. one or more of the following membrane adhesion molecules: DSG-3, MINK1, ASAP2, ZNF185, TJP2, SVIL, MYH10, LAMC1, TANC1, ILKAP, FAM129B, PALLD, PTRF, PDLIM5, TNS4, GAK, LANCL1, MYH9, THBS1, LRRC16A, FER, SYNE2, SYNE1, ENAH, PKP2, SNTB2, PARVA, PRKD2, KDF1, COL7A1, CSK, ARPC2, SNAP23, JUP, ARF1, NPTN, MTDH, ACTN1, CFL1, LAMA3, DSC3, STOML2, FSCN1, AP2A1, ACTN4, NDRG1, LAMC2, LIMA1, FERMT1, PI4K2A, OCLN, KRT1, RAP1A, FAP, ARFGEF2, FAM120A, CD44, CIB1, COL12A1, DST, ATP1B1, ATAD1, LAMB1, CDH4, FAT2, PVR, CD109, CDH13, PKP4, CD63, PCDH1, GJA1, MPST, PSEN1, CLCA2, MELTF, SLC7A5, FOCAD, MISP, VEZT, EPHB4, RUSC1, RAB13.

In yet still a further aspect of the invention there is provided a method of prognosing a risk of progression from a pre-invasive epithelial neoplasia associated with the glandular epithelium in a mammal, said method comprising screening for the level of expression of Stefin A in myoepithelial cells and one or more of:

(i) Stromal cells
(ii) Glandular epithelial cells
wherein a decrease in the level of Stefin A expression relative to a control level is indicative of an increased risk of progression of the neoplasia.

Preferably, in the level of expression of Stefin A is assessed by detecting RNA transcripts, cDNA transcribed from the RNA transcripts and/or a protein expression product from the RNA transcripts and/or by detecting cathepsin protease activity, in particular cathepsin B, wherein increased cathepsin protease activity is indicative of a decrease in the level of Stefin A expression and an increased risk of progression of the neoplasia.

BRIEF DESCRIPTION OF THE DRAWINGS

FIG. 7 3D co-culture control experiments. (A) siRNA knockdown of stefin A in N1ME myoepithelial cell line as shown by immunoblotting, compared to siRNA non-targeting control. GAPDH used as loading control. (B) siRNA stefin A knockdown N1ME cells produced results comparable to TALEN stefin A low cells (FIG. 6) when co-cultured with MDA-MB-231. (Bi) Bright field images of MDA-MB-231 (unlabeled) co-cultured with/without myoepithelial cells. (Bii) Confocal images, rendered in Imaris, of MDA-MB-231 Hoechst stained (blue) alone or co-cultured with myoepithelial cells (red). (Biii) Quantification of invasive outgrowths. Invasiveness of 3D cultures was determined by calculating the ratio between the perimeter and convex hull of each colony. A value of 1 indicated a smooth object, as the value moves away from 1 towards zero the number and/or size of protrusions from the colony was increased. Frequency distribution of population data under log Gaussian fit. A bin center closer to 1 indicated a smooth surface. Comparison of center of each curve was statistically analyzed. *p<0.05, p<0.01, **p<0.0001. n=3. (C) N1ME myoepithelial cells (WT) can revert the invasive outgrowths of another invasive breast cancer cell line, CAL-120. N1ME stefin A low myoepithelial cells failed to inhibit the invasive outgrowths of CAL-120 cells to the extent observed with WT myoepithelial cells. (Ci) Bright field images of CAL-120 cells alone or co-cultured with myoepithelial WT or stefin A low cells. (Cii) Confocal images, rendered in Imaris, of CAL-120 Hoechst stained (blue) alone or co-cultured with myoepithelial WT or stefin A low cells (red). (Ciii) Quantification of invasive outgrowths as previously described. (D) Bright field images of MDA-MB-231 cells grown alone or in co-culture with myoepithelial WT or stefin A low cells in 2D do not exhibit spheroid formation. Scale bars represent 200 μm. (E) Conditioned media from N1ME, DCIS and MDA-MB-231 cells were electrophoretically separated (SDS-PAGE) and immunoblotted for stefin A.

DETAILED DESCRIPTION OF THE INVENTION

Figure 1:
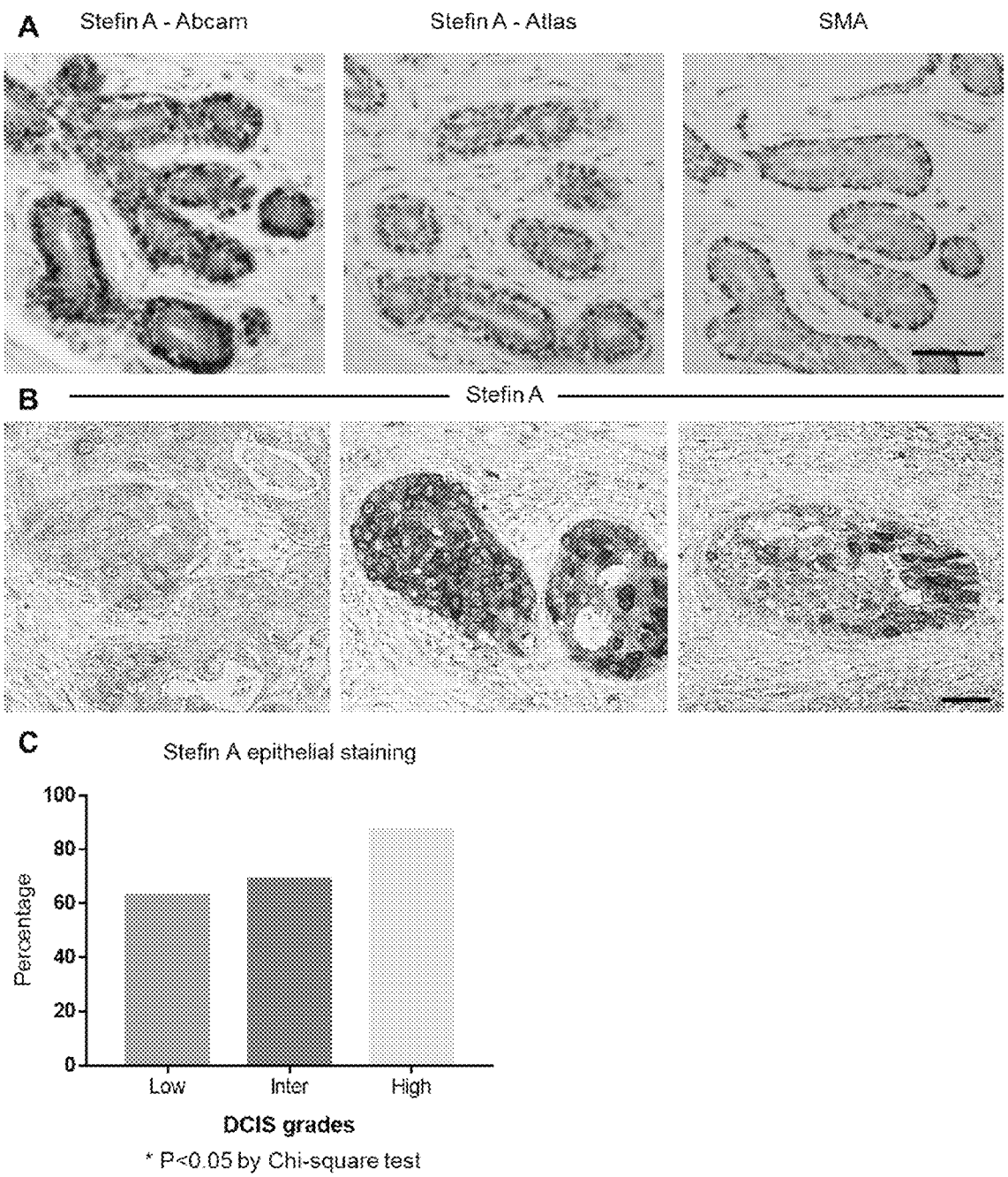
FIG. 1 Expression of stefin A in DCIS tissue. Sections of formalin-fixed, paraffin-embedded tissue were stained with rabbit anti-human stefin A or SMA and visualized with DAB (brown). All sections were counterstained with hematoxylin (blue nuclei). (A) Expression of stefin A as confirmed by two independent antibodies (Abcam and Atlas) in myoepithelial cells of normal ducts. Alpha-smooth muscle actin (SMA) was used as a myoepithelial marker. (B) IHC detection of stefin A was observed in the tumor cells of DCIS lesions with absent myoepithelial stefin A expression. Scale bars represents 50 μm. (C) Epithelial stefin A expression was pathologist scored and compared between grades (inter, intermediate). The percentage of DCIS cases that scored positive for stefin is shown. Chisquare test comparing percentage positivity between DCIS grades *$p<0.05$.

The present invention is predicated, in part, on the determination that a decreased level of Stefin A expression in myoepithelial cells, relative to normal levels, is an indicator of an increased risk of neoplastic progression in a patient exhibiting a pre-invasive neoplasm. For example, prognosing the risk of progression from a pre-invasive breast neoplasia to an invasive neoplasia is enabled, as is the risk of relapse (recurrence) in a patient who has completed treatment. Most significantly, however is the determination that one can identify which patients exhibiting pre-invasive neoplasia need not undergo any form of treatment. This finding has therefore facilitated the development of a method of screening a patient to prognose likely risk of neoplasia progression.

Accordingly, one aspect of the present invention is directed to a method of prognosing a risk of progression from a pre-invasive epithelial neoplasia associated with the glandular epithelium in a mammal, said method comprising screening for the level of expression of Stefin A in myoepithelial cells wherein a decrease in the level of Stefin A expression relative to a control level is indicative of an increased risk of progression.

Reference to a "neoplasia" should be understood as a reference to a condition characterised by the presence or development of encapsulated or unencapsulated growths or aggregates of neoplastic cells. Reference to a "neoplastic cell" should be understood as a reference to a cell exhibiting abnormal growth. Reference to a "neoplasm" should be understood as a reference to a lesion, tumour or other encapsulated or unencapsulated mass or other form of growth or cellular aggregate which comprises neoplastic cells. The term "growth" should be understood in its broadest sense and includes reference to enlargement of neoplastic cell size as well as proliferation.

The phrase "abnormal growth" in this context is intended as a reference to cell growth which, relative to normal cell growth, exhibits one or more of an increase in individual cell size and nuclear/cytoplasmic ratio, an increase in the rate of cell division, an increase in the number of cell divisions, a decrease in the length of the period of cell division, an increase in the frequency of periods of cell division or uncontrolled proliferation and evasion of apoptosis. Without limiting the present invention in any way, the common medical meaning of the term "neoplasia" refers to "new cell growth" that results as a loss of responsiveness to normal growth controls, eg. to neoplastic cell growth, including cancer.

The term "carcinoma" is recognised by those skilled in the art to refer to malignancies of epithelial or endocrine tissues. Exemplary carcinomas include those forming from tissue of the breast. The term also includes carcinosarcomas, e.g. which include malignant tumours composed of carcinomatous and sarcomatous tissues. An "adenocarcinoma" refers to a carcinoma derived from glandular tissue or in which the tumour cells form recognisable glandular structures.

Reference to "epithelium" or "epithelial cell" should be understood as a reference to the cell type which can form epithelium and which is derived from either of the endoderm or the ectoderm. Epithelium consists of closely packed cells which form a sheet and generally comprise very little intercellular material. Epithelial cell types can vary thereby giving rise to various types of epithelia including squamous, cuboidal, columnar and ciliated epithelia. There are three main types of epithelial tissue, these being covering/lining epithelium, glandular epithelium and sensory epithelium, being the epithelium which can form part of the sensory organs. The phrase "epithelial cells" should also be understood as a reference to cells which exhibit one or more of the morphology, phenotype and/or functional activity of epithelial cells and is also a reference to mutants or variants thereof. "Variants" include, but are not limited to, cells exhibiting some but not all of the morphological or phenotypic features or functional activities of epithelial cells at any differentiative stage of development. "Mutants" include, but are not limited to, epithelial cells which have been naturally or non-naturally modified. It should also be understood that the epithelial cells of the present invention may be at any differentiative stage of development. In one embodiment, said breast neoplasia is an epithelial neoplasia.

Reference to the subject epithelial neoplasia being "associated with" the glandular epithelium should be understood as a reference to the epithelial neoplasm being a neoplasm of the glandular epithelium or a neoplasm of epithelial cells which are in close physical proximity to glandular epithelium. Examples of tissues which comprise glandular epithelium include, but are not limited to, breast, prostate, colon, stomach, sweat glands, sebaceous glands, duodenal glands, liver, pancreas, thyroid, anterior pituitary and adrenol.

In one embodiment, said neoplasia is a breast neoplasia.

The neoplasia of one embodiment of the present invention is a neoplasia of the breast tissue. Reference to "breast tissue" should be understood as a reference to cells which form part of the breast. Without limiting the present invention to any one theory or mode of action, the breast gland is a structurally dynamic organ which varies with age, menstrual cycle and reproductive status. It is a branched tubuloalveolar gland exhibiting secretory acinii which are grouped with inner lobules and drain into intralobular ducts which in turn drain into interlobular ducts. The lobules are organised into 15-20 lobes, each of which empty into separate lactiferous sinuses and from there into lactiferous ducts. The intralobular stroma consists of a loose connective tissue with a zone of hormone sensitive fibroblasts surrounding the lobular epithelial components. These are thought to take part in epithelial/basement membrane/stromal inductive interactions during morphogenesis and differentiation. Since the breast undergoes unique differentiative and proliferative development during the various life cycle stages of an individual, it should be understood that reference to breast tissue, in particular ductal tissue and myoepithelial cells, is a reference to the epithelial cells and tissue comprising the breast at any stage of its development including prepubescent, pubescent, prenatal, postnatal/lactating and post-menopausal stages. In this regard, it should also be understood that any given population of cells or tissue of interest may only be transiently present in the mammary gland, such as those which are generated during pregnancy for the purpose of facilitating lactation.

According to this embodiment there is provided a method of prognosing a risk of progression from a pre-invasive breast epithelial neoplasia in a mammal, said method comprising screening for the level of expression of Stefin A in breast myoepithelial cells wherein a decrease in the level Stefin A expression relative to a control level is indicative of an increased risk of progression.

Without limiting the present invention to any one theory or mode of action, epithelial neoplasias are often referred to as carcinomas, since carcinomas are typically a neoplasia of the epithelial cell. More specifically, the subject breast neoplasia may be adenocarcinoma, this being a carcinoma which starts in glandular tissue, such as breast tissue.

In accordance with this embodiment there is provided a method of prognosing a risk of progression from a pre-invasive breast carcinoma in a mammal, said method comprising screening for the level of expression of Stefin A in breast myoepithelial cells wherein a decrease in the level of Stefin A expression relative to a control level is indicative of an increased risk of progression.

In one embodiment, said neoplasia is a neoplasia of the breast lobules or ducts.

According to this embodiment there is provided a method of prognosing a risk of progression from a pre-invasive breast lobular or ductal neoplasia in a mammal, said method comprising screening for the level of expression of Stefin A in breast myoepithelial cells wherein a decrease in the level of Stefin A expression relative to a control level is indicative of an increased risk of progression.

Still more preferably, there is provided a method of prognosing a risk of progression from a pre-invasive breast ductal neoplasia in a mammal, said method comprising screening for the level of expression of Stefin A in breast ductal myoepithelial cells wherein a decrease in the level of Stefin A expression relative to a control level is indicative of an increased risk of progression.

Still more preferably, said myoepithelial cells are localised to the same tissue region as the neoplasia and, in a particular embodiment, are located adjacent or proximal to the neoplasia.

As detailed hereinbefore the method of the present invention is directed to prognosing the risk of a pre-invasive breast neoplasia progressing. In this regard, reference to a "pre-invasive" neoplasia should be understood as reference to a neoplasia where the neoplastic cells have not yet migrated away from their point of origin into the surrounding breast tissue. That is, the neoplasia is still contained within the duct or lobule and has not migrated through the wall of the duct/lobule (at which point it is referred to as "invasive"). Such neoplasias are early stage and are commonly referred to a "pre-invasive", "early stage", "in situ", "non-invasive" and "pre-cancerous". These neoplasias are generally classified as Stage 0. Reference to "pre-invasive" should therefore be understood to encompass reference to neoplasias commonly described by all of the above terms. It would be appreciated by the skilled person that pre-invasive breast neoplasias are usually diffuse or unencapsulated aggregations of neoplastic cells and have not yet formed tumours (referred to as "lesions"). However, it should be understood that the present invention also encompasses the situation where the pre-invasive neoplastic cells have divided sufficiently such that a tumour has formed within the duct or lobule, but the cells of which have not yet migrated through the wall of the duct and thereby become invasive. In the context of the present invention, any form of association of neoplastic cells which have not yet migrated across the wall of the duct/lobule should be understood as falling within the definition of "pre-invasive". It would be appreciated by the person of skill in the art that the transition of a breast neoplasia from pre-invasive to invasive (whereby the neoplasia infiltrates the surrounding breast tissue) is the forerunner to potential further spread beyond the breast and therefore the transition to neoplastic disease.

Pre-invasive neoplasias of the breast include, but are not limited to hyperplasia, lobular carcinoma in situ (LCIS) (starting in breast lobules/end buds) and ductal carcinoma in situ (DCIS) (starting in ductal epithelial cells). To the extent that the subject neoplasia is DCIS, the skilled person would appreciate that DCIS can be further catergorised by:

Grade: low, medium/intermediate or high-grade lesions; and

Comedo histology: comedo vs non-comedo (solid, cribform, papillary) forms.

Without limiting the present invention to any one theory or mode of action, pre-invasive neoplasms may be identified, monitored or assessed through clinical screening or diagnostic procedures, including, but not limited to, palpation, biopsy, cell proliferation index, mammography, digital mammography, ultrasonography, computed tomography (CT), magnetic resonance imaging (MM), positron emission tomography (PET), radiography, radionuclide evaluation, CT- or MM-guided aspiration cytology, and imaging-guided needle biopsy, among others. Such diagnostic techniques are well known to those skilled in the art. Once a pre-invasive neoplasia has been identified, a sample for testing will usually be harvested. This may be achieved by any suitable method and is discussed in more detail hereinafter.

As detailed hereinbefore, the development of the present invention has enabled a means of prognosing the progression from a pre-invasive breast neoplasia. Reference to "prognosis" should be understood as a reference to predicting the relative risk of progression of a breast neoplasia. By "progression" is meant either the transition to an invasive phenotype or else the likelihood of subsequent relapse (recurrence) in a patient who has been treated. With reference to the "transition" to an invasive phenotype, it should be understood that this extends to the earliest stage of transition, this often referred to as "initiation" wherein actual invasion has not yet occurred but cellular change has commenced in the neoplastic epithelial cells and/or the myoepithelial cells which may lead to the onset of invasion. This may be particularly useful, for example, in screening patients who have never had cancer or are treated and cancer free and are at a high risk (eg. such as those with high breast density or a family link). To the extent that relapse occurs, this may be either "local" relapse, this corresponding to the development of a further neoplasia in or around the site of the original neoplasia, or "distant" relapse meaning the onset of an invasive breast neoplasia, potentially progressing to metastatic disease. Neoplasm growth occurring at a site distant from the site of the original neoplasm includes, but is not limited to, bones, brain, lung, liver, bladder, cervix, colon, prostate, pancreas, thyroid, kidney and skin.

Accordingly, in one embodiment said neoplasia progression is the transition to an invasive phenotype.

In another embodiment, said neoplasia progression is relapse.

Reference to "risk" of progression should be understood to be a reference to the probability or likelihood that progression will occur. It should be understood, however, that progression may not necessarily occur in all cases. The method of the present invention is providing an estimation as to the cohort of patients in respect of which progression is significantly more likely to occur than the cohort of patients in respect of which progression is not likely to occur. Accordingly, this method provides extremely valuable information which can form the basis of decisions regarding treatment and ongoing monitoring. For example, in patients exhibiting unchanged levels of myoepithelial Stefin A expression, one may elect to not subject the patient to treatment to remove the neoplasia or, if surgical excision has already occurred, follow up radiotherapy, chemotherapy, cysteine cathepsin inhibitors, and targeted antibody therapy.

Reference to cysteine cathepsin inhibitors should be understood as a reference to all forms of cysteine cathepsin inhibitors and to fragments and homologs thereof. It should be understood to include cathepsin B-selective inhibitor CA-074.

Reference to "Stefin A" should be understood as a reference to all forms of Stefin A and to fragments and mutants thereof. It should be understood to include reference to any protein encoded by the Stefin A gene including precursor forms of Stefin A which may be generated. Reference to "Stefin A" is not intended to be limiting and should be read as including reference to all isoforms of Stefin A which may arise from alternative splicing or Stefin A mRNA or mutant or polymorphic forms of Stefin A. Without limiting the present invention to any one theory or mode of action, Stefin A is a physiological inhibitor of the cysteine proteases and belongs to family I of the cystatin superfamily of inhibitors or Stefin subgroup of the 3 described cystatin families. It is an 11 kDa single chain intracellular cysteine protease inhibitor capable of inhibiting papain and cathepsins B, H and L, as well as the cysteine protease activity of the major house dust mite allergen Der p 1. The skilled person would appreciate that Stefin A is also known as cystatin A.

The method of the present invention is predicated on the correlation of Stefin A levels in patients with a control level of this molecule. The control level may either be the "normal" level of Stefin A in the myoepithelial cells of a corresponding biological sample of a patient who has not developed a pre-invasive neoplasm, or it may correspond to an earlier Stefin A level determined from the patient in issue. This latter analysis is a form of relative analysis (which may nevertheless also be assessed relative to "normal" levels) which provides information in relation to the patient over time, such as the context of on going monitoring. It would be appreciated that in terms of a "normal" level, it is likely to be most convenient to analyse the test results relative to a standard result which reflects individual or collective results obtained from healthy individuals. This is in fact the preferred method of analysis since it enables the design of kits which require the collection and analysis of a single biological sample, being a test sample of interest. The standard results which provide the normal level may be calculated by any suitable means which would be well known to the person of skill in the art. For example, a population of normal biological samples can be assessed in terms of the level of Stefin A expression in breast myoepithelial cells, thereby providing a standard value or range of values against which all future test samples are analysed. It should also be understood that the normal level may be determined from the subjects of a specific cohort and for use with respect to test samples derived from that cohort. Accordingly, there may be determined a number of standard values or ranges which correspond to cohorts which differ in respect of characteristics such as age, gender, ethnicity or health status. Said "normal level" may be a discrete level or a range of levels.

In a further embodiment, the present invention provides a method of prognosing a risk of progression from a pre-invasive breast neoplasm in a mammal, said method comprising screening for the level of expression of Stefin A in breast myoepithelial cells wherein a decrease in the level of Stefin A expression relative to a normal level is indicative of an increased risk of progression.

In another embodiment there is provided a method of monitoring a patient for a risk of progression from a pre-invasive breast neoplasm in an mammal, said method comprising screening for the level of expression of Stefin A in breast myoepithelial cells wherein a decrease in the level of Stefin A expression relative to a previous test result level is indicative of an increased risk of progression.

In accordance with these embodiments said breast neoplasm is an epithelial neoplasm, more particularly a ductal or lobular neoplasm.

Still more particularly, said myoepithelial cells are ductal myoepithelial cells, more particularly said ductal myoepithelial cells are located adjacent or proximally to the pre-invasive neoplasm.

In yet another embodiment, said progression is either relapse or transition to an invasive phenotype.

In still yet another embodiment, the present invention provides a method of prognosing or monitoring for the risk of onset of an invasive epithelial neoplasia associated with the glandular epithelium wherein a decrease in the level of Stefin A expression in myoepithelial cells relative to a normal level is indicative of an increased risk of the onset of an invasive neoplasia.

In one embodiment, said neoplasia is a breast neoplasia.

In still another embodiment, the present invention provides a method of prognosis and/or monitoring a patient risk of progression from a pre-invasive breast neoplasia in a mammal, said method comprising assessing the level of expression of Stefin A and one or more markers in myoepithelial cells wherein the one or more other markers include:
a) Cysteine cathepsin protease; and/or
b) one or more of the following membrane adhesion molecules:
  (i) DSG3; and/or
  (ii) MINK1, ASAP2, ZNF185, TJP2, SVIL, MYH10, LAMC1, TANC1, ILKAP, FAM129B, PALLD, PTRF, PDLIM5, TNS4, GAK, LANCL1, MYH9, THBS1, LRRC16A, FER, SYNE2, SYNE1, ENAH, PKP2, SNTB2, PARVA, PRKD2, KDF1, COL7A1, CSK, ARPC2, SNAP23, JUP, ARF1, NPTN, MTDH, ACTN1, CFL1, LAMA3, DSC3, STOML2, FSCN1, AP2A1, ACTN4, NDRG1, LAMC2, LIMA1, FERMT1, PI4K2A, OCLN, KRT1, RAP1A, FAP, ARFGEF2, FAM120A, CD44, CIB1, COL12A1, DST, ATP1B1, ATAD1, LAMB1, CDH4, FAT2, PVR, CD109, CDH13, PKP4, CD63, PCDH1, GJA1, MPST, PSEN1, CLCA2, MELTF, SLC7A5, FOCAD, MISP, VEZT, EPHB4, RUSC1, RAB13.

In a further embodiment, the present invention provides a method of further screening for other variables including estrogen receptor, progesterone receptor and human epidermal growth factor receptor (HER2).

In a further embodiment, the present invention provides a method of prognosing a risk of progression from a pre-invasive epithelial neoplasia associated with the glandular epithelium in a mammal, said method comprising screening for the level of expression of Stefin A in myoepithelial cells and one or more of:
a) Stromal cells
b) Glandular epithelial cells
wherein a decrease in the level of Stefin A expression relative to a control level is indicative of an increased risk of progression of the neoplasia.

The breast myoepithelial cells which are tested in accordance with the method of the present invention are preferably provided in a biological sample which has been harvested from the subject mammal. In this regard, reference to a "biological sample" should be understood as a reference to any sample of biological material derived from a mammal such as, but not limited to, cellular material, tissue biopsy specimens or any other sample type which would comprise myoepithelial cells. The biological sample which is tested according to the method of the present invention may be tested directly or may require some form of treatment prior to testing, such as cellular enrichment.

The biological sample may be directly tested or else all or some of the protein or nucleic acid material present in the biological sample may be isolated prior to testing. In yet another example, the sample may be purified or otherwise enriched prior to analysis. For example, to the extent that a biological sample comprises a very diverse cell population, it may be desirable to select out the myoepithelial cells. Alternatively, tissue blocks may be prepared and sectioned for screening. It is within the scope of the present invention for the biological sample to be pre-treated prior to testing, for example inactivation of live virus. It should also be understood that the biological sample may be freshly harvested or it may have been stored (for example by freezing) prior to testing or otherwise treated prior to testing. In terms of the method of the present invention, breast tissue biopsy samples are particularly convenient to test since they can be sectioned and stained. This enables the architecture of the breast tissue sample to be visualised and thereby the Stefin A expression of the myoepithelial cells to be easily assessed. However, in another example one might harvest cells from the site of the lesion and select out the myoepithelial cells for analysing such as via FACS analysis. The choice of what type of sample is most suitable for testing in accordance with the method disclosed herein will be dependent on the nature of the situation.

Reference to "expression" should be understood as a reference to the transcription and/or translation of a nucleic acid molecule to produce a protein. The term "protein" should be understood to encompass peptides, polypeptides and proteins (including protein fragments). The Stefin A protein may be glycosylated or unglycosylated and/or may contain a range of other molecules fused, linked, bound or otherwise associated to the protein such as amino acids, lipids, carbohydrates or other peptides, polypeptides or proteins. Reference herein to a "protein" includes a protein comprising a sequence of amino acids as well as a protein associated with other molecules such as amino acids, lipids, carbohydrates or other peptides, polypeptides or proteins. Reference to "RNA" should be understood to encompass reference to any form of RNA, such as primary RNA or mRNA. Without limiting the present invention in any way, the modulation of gene transcription leading to increased or decreased RNA synthesis will also correlate with the translation of these RNA transcripts (such as mRNA) to a protein product. Although the preferred method is to screen for the Stefin A protein product, it should be understood that the present invention is not limited in this regard and extends to screening for any other form of expression product such as, for example, RNA, mRNA or cDNA. It is well within the skill of the person of skill in the art to design methodology directed to screening for protein, cDNA or RNA.

Reference to a "fragment" of Stefin A should be understood as a reference to a portion of the subject protein or nucleic acid molecule. This is particularly relevant with respect to screening for RNA levels since these are inherently unstable molecules and may be screened for in samples which express high levels of enzymes. In this case the subject RNA is likely to have been degraded or otherwise fragmented. One may therefore actually be detecting fragments of the subject RNA molecule, which fragments are identified by virtue of the use of a suitably specific probe.

A "mutant" of Stefin A should be understood to mean a Stefin A molecule which exhibit mutations in the amino acid or nucleic acid sequence.

The reference to "mammal" should be understood to include humans, primates, livestock animals (eg. horses, cattle, sheep, pigs, donkeys), laboratory test animals (eg. mice, rats, guinea pigs), companion animals (eg. dogs, cats) and captive wild animals (eg. kangaroos, deer, foxes). Preferably, the mammal is a human. In this regard, it should also be understood that although the individuals who are tested in accordance with the method of the present invention are most likely women, breast epithelial carcinomas are also known to affect men. Although this is rare, when it does occur it is usually a ductal carcinoma. Accordingly, the present method has application to screening both women and men.

As detailed hereinbefore, one of the particularly surprising determinations in relation to the present invention is the fact that Stefin A expression in myoepithelial cells is predictive of whether or not a patient presenting with a pre-invasive breast neoplasia need undergo treatment such as surgery, radiation therapy and/or chemotherapy.

According to this embodiment there is provided a method of informing treatment regimes or determining whether to treat a mammal presenting with a pre-invasive breast neoplasia, said method comprising screening for the level of expression of Stefin A in breast myoepithelial cells wherein:
(i) a decrease in the level of Stefin A expression relative to a normal level is indicative of an increased risk of progression and the need for treatment; or
(ii) no change in relation to the level of Stefin A expression relative to a normal level is indicative of a low risk of progression and no need for treatment.

In yet another embodiment there is provided a method of determining whether to treat a mammal being monitored for the progression from a pre-invasive breast neoplasia, said method comprising screening for the level of expression of Stefin A in breast myoepithelial cells wherein a decrease in the level of Stefin A expression relative to a previous test result level is indicative of an increased risk of progression and the need for treatment.

In one embodiment, said treatment includes:
a) Cysteine cathepsin inhibitors;
b) Surgical excision;
c) Radiotherapy;
d) Chemotherapy;
e) Targeted antibody therapy; and/or
f) Endocrine therapy In one embodiment, said neoplasia is a neoplasia of the breast lobules or ducts.

In accordance with these embodiments said breast neoplasm is an epithelial neoplasm, more particularly a ductal or lobular neoplasm.

Still more particularly, said myoepithelial cells or ductal myoepithelial cells, more particularly said ductal myoepithelial cells located adjacent or proximally to the pre-invasive neoplasm.

In yet another embodiment, said progression is either relapse or transition to an invasive phenotype.

In terms of monitoring a patient to determine an appropriate treatment regime, it would be understood that the patient may be one who has been diagnosed with a low risk pre-invasive neoplasia and is therefore not undergoing any form of treatment. In this case one is monitoring for changes to myoepithelial Stefin A levels which would indicate imminent transition to an invasive phenotype. In another example, one may be screening a patient who has previously undergone treatment and the transition to potential relapse/recurrence is under watch. In still another example, one may be monitoring a patient who has never had neoplasia but is at high risk due to, for example, familial history.

In the context of the aspects and embodiments of the invention hereinbefore described, it should also be understood that in addition to screening for Stefin A levels, per se, the skilled person could also screen for the ratio of Stefin A to the level of its target proteins, these being the cysteine cathepsins. This could inform the skilled person of the overall cathepsin protease activity in a particular lesion.

In a preferred embodiment, the level of expression of Stefin A in myoepithelial cells is assessed by detecting cathepsin protease activity, in particular cathepsin B, wherein increased cathepsin protease activity is indicative of a decrease in the level of Stefin A expression and an increased risk of progression of the neoplasia.

Screening for the level of expression of Stefin A may be achieved by any suitable method which would be well known to the person of skill in the art. In this regard, it should be understood that reference to screening for the level of protein and/or gene expression in a "mammal" is intended as a reference to the use of any suitable technique which will provide information in relation to the level of expression of Stefin A in the relevant tissue of the mammal.

These screening techniques include both in vivo screening techniques, as hereinafter described, as well as the in vitro techniques which are applied to a biological sample extracted from said mammal.

Since the present invention is predicated on screening for changes to the level of Stefin A, such changes can in fact be screened for at the protein level or at the RNA or cDNA level, such as by screening for decreases in the level of the relevant mRNA transcripts. The person of skill in the art will determine the most appropriate means of analysis in any given situation. However it is generally preferred that screening is performed in the context of protein molecules due to the relative simplicity of the techniques which are likely to be utilised. Nevertheless in certain situations, and in the context of particular biological samples, it may be desirable or otherwise useful to directly analyse RNA translation.

As described above, means of screening for changes to levels Stefin A (herein referred to as "the marker") in an individual, or biological sample derived therefrom, can be achieved by any suitable method, which would be well known to the person of skill in the art, such as but not limited to:

(i) Measurement of Altered Stefin a Protein Levels in Cell or Tissue Extracts, for Example by Immunoassay Utilising Immunointeractive Molecule.

Testing for proteinaceous marker expression product in a biological sample from a patient can be performed by any one of a number of suitable methods which are well known to those skilled in the art. Examples of suitable methods include, but are not limited to, antibody screening of tissue sections or biopsy specimens. To the extent that antibody based methods of diagnosis are used, the presence of the marker protein may be determined in a number of ways such as by immunohistochemistry, radioimmunoassay, immunochromographic techniques, Western blotting, ELISA or flow cytometry procedures. These, of course, include direct binding of a labelled antibody to a target. Additionally, these assays also include both single-site and two-site or sandwich assays of the non-competitive types, as well as in the traditional competitive binding assays.

Immunohistochemical staining of tissue sections is particularly useful with biopsy samples. A number of variations of the immunohistochemical assay technique exist, and all are intended to be encompassed by the present invention. Briefly, in a typical immunohistochemical assay, a solution of paraformaldehyde is often used to fix the tissue samples, but other methods may be used. The tissue may then be sliced or used whole, depending upon the purpose of the experiment or the tissue itself. Before sectioning, the tissue sample may be embedded in a medium, like paraffin wax or cryomedia. Sections can be sliced on a variety of instruments, most commonly a microtome or cryostat, and are sliced at a range of 4-40 μm. The slices are then mounted on slides, dehydrated using alcohol washes of increasing concentrations (e.g., 50%, 75%, 90%, 95%, 100%), and cleared using a detergent like xylene before being imaged under a microscope.

Depending on the method of fixation and tissue preservation, the sample may require additional steps to make the marker available for antibody binding, including deparaffinization and antigen retrieval. For formalin-fixed paraffin-embedded tissues, antigen-retrieval is often necessary, and involves pre-treating the sections with heat or protease. These steps may make the difference between the target marker staining or not staining.

Detecting a target antigen with antibodies, whether in the context of a tissue section of a single cell suspension is usually a multi-step process and both primary and secondary antibodies are diluted into a buffer to help stabilize the antibody, promote the uniform dissemination throughout the sample and discourage nonspecific binding. The sample is rinsed in between antibody application to remove unbound antibodies and also to remove antibodies that are weakly bound to nonspecific sites. Nevertheless, single step methods can also be performed.

The reporter molecule which is used may be any molecule which, by its chemical nature, provides an analytically identifiable signal which allows the detection of antigen-bound antibody. Detection may be either qualitative or quantitative. The reporter molecule may be selected from a group including a chromogen, a catalyst, an enzyme, a fluorochrome, a chemiluminescent molecule, a paramagnetic ion, a lanthanide ion such as Europium ($Eu^{34}$), a radioisotope including other nuclear tags and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like. A large number of enzymes suitable for use as reporter molecules is disclosed in U.S. Pat. Nos. U.S. Pat. Nos. 4,366,241, 4,843,000, and 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. No. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218. Alternately, fluorescent compounds, such as fluorescein, rhodamine or lanthanide chelates, such as europium, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

(ii) In Vivo Detection

Molecular Imaging may be used following administration of imaging probes or reagents capable of disclosing altered expression of Stefin A. Molecular imaging (Moore et al., BBA, 1402:239-249, 1988; Weissleder et al., Nature Medicine 6:351-355, 2000) is the in vivo imaging of molecular expression that correlates with the macro-features currently visualized using "classical" diagnostic imaging techniques such as X-Ray, computed tomography (CT), Mill, Positron Emission Tomography (PET) or endoscopy.

(iii) Detection of down-regulation of RNA expression in the cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., Clinical Chemistry 48:9 1398-1405, 2002), RNA sequencing, NextGen sequencing, amplification, array technologies or non-PCR amplification techniques, including isothermal techniques.

For example, to detect Stefin A encoding RNA transcripts, RNA is isolate from the myoepithelial cells of the patient. RNA can be isolated by methods known in the art, e.g. using TRIZOL™ reagent (GIBCO-BRL/Life Technologies, Gaithersburg, Md.), Oligo-dT or random-sequence oligonucleotides, as well as sequence-specific oligonucleotides can be employed as a primer in a reverse transcriptase reaction to prepare first-strand cDNAs from the isolated RNA. Resultant first-strand cDNAs are then amplified with sequence-specific oligonucleotides in PCR reactions to yield an amplified product.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences and cDNA transcribed from total cellular RNA. See generally Mullis et al., 1987; (Methods Enzymol 155:335-50) and Erlich, 1989 (J Clin Immunol 9(6):437-47). Thus, amplification of specific nucleic acid sequences by PCR relies upon oligonucleotides or "primers" having conserved nucleotide sequences wherein the conserved sequences are deduced from alignments of related gene or protein sequences. For example, one primer is prepared which is predicted to anneal to the antisense strand and another primer prepared which is predicted to anneal to the sense strand of a cDNA molecule which encodes Stefin A.

To detect the amplified product, the reaction mixture is typically subjected to agarose gel electrophoresis or other convenient separation technique and the relative presence of Stefin A specific amplified nucleic acid detected. For example, the Stefin A amplified nucleic acid may be detected using Southern hybridization with a specific oligonucleotide probe or comparing its electrophoretic mobility with nucleic acid standards of known molecular weight. Isolation, purification and characterization of the amplified telomerase nucleic acid may be accomplished by excising or eluting the fragment from the gel (for example, see references Lawn et al., 1981; Goeddel et al., 1980), cloning the amplified product into a cloning site of a suitable vector, such as the pCRII vector (Invitrogen), sequencing the cloned insert and comparing the sequence to the known sequence of Stefin A. The relative amounts of Stefin A mRNA and cDNA can then be determined.

In terms of the assessment of expression profiles of RNA, by array technologies (Alon et al., Proc. Natl. Acad. Sci. USA: 96, 6745-6750, June 1999), a "microarray" is a linear or multi-dimensional array of preferably discrete regions, each having a defined area, formed on the surface of a solid support. The density of the discrete regions on a microarray is determined by the total numbers of target polynucleotides to be detected on the surface of a single solid phase support. In one example, RNA from the sample of interest is subjected to reverse transcription to obtain labelled cDNA. See U.S. Pat. No. 6,410,229 (Lockhart et al.) The cDNA is then hybridized to oligonucleotides or cDNAs of known sequence arrayed on a chip or other surface in a known order. In another example, the RNA is isolated from a biological sample and hybridised to a chip on which are anchored cDNA probes. The location of the oligonucleotide to which the labelled cDNA hybridizes provides sequence information on the cDNA, while the amount of labelled hybridized RNA or cDNA provides an estimate of the relative representation of the RNA or cDNA of interest. See Schena, et al. Science 270:467-470 (1995). For example, use of a cDNA microarray to analyze gene expression patterns in human cancer is described by DeRisi, et al. (Nature Genetics 14:457-460 (1996)).

As detailed above, any suitable technique may be utilised to detect the Stefin A or its encoding nucleic acid molecule. The nature of the technique which is selected for use will largely determine the type of biological sample which is required for analysis. Such determinations are well within the scope of the person of skill in the art. Typical samples which one may seek to analyse are biopsy samples.

The present invention is further described by reference to the following non-limiting examples.

Example 1

Analysis of Stefin A expression in a cohort of 200 patient samples spanning normal, hyperplasia and low, intermediate and high grade DCIS lesions has revealed that the expression of Stefin A is significantly reduced with increasing DCIS grade. The loss of Stefin A in high grade DCIS lesions, those more likely to progress to invasive carcinoma, indicates that myoepithelial Stefin A suppresses the DCIS to invasive carcinoma transition. In summary a 3D culture system has been used to test this, as described below Method and Materials
Immunohistochemistry (IHC)

For human tissues, normal breast sections and primary breast carcinoma samples were obtained from Sandra O'Toole at the Royal Prince Alfred Hospital (RPAH) either as full-faced slides (for the micro-invasive carcinoma) or in a tissue microarray (TMA) (Zardawi et al.). The use of archived human tissues was approved by the HREC of RPAH (approval number X15-0388 (SSA/16/RPAH/397)). Sections (formalin-fixed, paraffin embedded) were stained with 1 μg/ml anti-human stefin A (ABCAM, Cambridge, UK, ab61223), p63 (DAKO, Denmark, DAK-p63, following antigen retrieval), anti-human α-smooth muscle actin (ABCAM, ab66133) or with isotype control antibodies, overnight at 4° C. and detected with a biotin-conjugated secondary antibody (Vector Laboratories, CA, USA) for 1 hour at room temperature. Peroxidases were blocked and ABC reagent (Vector) and DAB peroxidase substrate kit (Vector) were used to visualize specific staining.

Stefin A staining patterns were confirmed with a second antibody (HPA001031, Atlas, Stockholm, Sweden). The patient samples were scored for the intensity of staining and percentage of cells (myoepithelial and tumor scored separately) that were stefin A positive. The H score (intensity× percentage) was then calculated.

Cell Culture

The DCIS cell line was maintained in Dulbecco's Modified Eagle Medium (DMEM): Nutrient Mix F-12/5% Fetal Bovine Serum (FBS)/1% penicillin/streptomycin. The MDA-MB-231, MDA-MB-231-GFP and CAL-120 cell lines were maintained in DMEM/10% FBS/1% penicillin/ streptomycin. The N1ME myoepithelial cell line was maintained in Mammary Epithelial Cell Growth Medium (MEGM) (LONZA, Switzerland, CC3151) with Single Quot supplements (LONZA, CC-4136). All cell lines were maintained at 37° C., 5% $CO_2$.

In 2013, MCF10DCIS.com (DCIS) (Miller et al.), MDA-MB-231 human breast carcinoma cells, and N1ME human myoepithelial cells (hTERT immortalized by K. Polyak, mCherry labelled by H. Duivenvoorden) were provided by B. Sloane. In 2014, MDA-MB-231 cells were obtained from ATCC and labelled with GFP by A. Möller. The CAL-120 human breast carcinoma cells were obtained from DSMZ by Dr. Elgene Lim in 2014. Cell lines were tested and authenticated by short tandem repeat (STR) profiling and mycoplasma tested in 2015 and 2016.

Gene-Editing Using Transcription Activator-Like Effector Nucleases (TALENs).

Transcription activator-like effector nucleases (TALENs) targeting the human stefin A initiation codon were designed using Zifit (Polyak, 2005), yielding a pair of arrays specific for the nucleotide sequences 5'-TCCAGCAAAGAAGCAATC and 5'TGGCCTCAGA-TAAGCCTC. Arrays were assembled according to Reyon, Tsai (4) and N1ME myoepithelial cherry labelled cells were transfected with the TALEN constructs and a limiting amount of pEGFP-N1 (Clontech) used as a marker for transfection (Gudjonsson, 2005). Double cherry/GFP positive cells were gated for single-cell sorting into 96 well plates (FACS Aria III, BD Biosciences). Western blotting was used to determine the presence of stefin A protein in the resulting clonal cell lines. The targeted genomic region was amplified from clones with low stefin A and sequenced to determine the TALEN-mediated insertions and deletions. The Fiji distribution of IMAGEJ (Schindelin et al., 2012) was used to calculate the intensity of protein bands on western blots relative to their respective loading control (βactin) and compared between each clone pair.

Short-Interfering RNA siRNA for stefin A (M-010020-01), Dsg3 (M-011646-01), E-cadherin (M-003877-02) and CD10 (M-005112-01) or OTP-NT non-targeting control (25 μm, Dharmacon, Colorado, USA) were transfected into the N1ME cell line using DharmaFect 3 (Dharmacon) and Opti-MEM (ThermoFisher, MA, USA). Forty-eight hours post-transfection, cells were seeded into 3D culture as described below. Remaining cells were lysed and western blotting techniques as described below were conducted.

3D Cell Culture

All 3D cultures were performed using CULTREX® (Trevigen, Gaithersburg, MD, 3433-005-01) similar to previously described (Mullins et al.). Briefly, 8 well chambers (THERMOFISHER, NUN155409) were coated with 100% CULTREX and allowed to solidify at 37° C. Cells (premixed at 1:1 ratio) were seeded on top of the solidified CULTREX and allowed to adhere for 60-90 minutes before 2% CULTREX in MEGM media (LONZA) was overlaid. Media was changed every 4 days unless otherwise stated. On day 7, Z-stacks were captured on a ZEISS LSM 780 inverted confocal microscope, and 3D-reconstructions were created using IMARIS. Inhibitor 3D studies were performed by the addition to the media of 50 μM of the highly selective cathepsin B inhibitor CA-074 (synthesized and purified in the Bogyo laboratory, CA) or the pan-cysteine cathepsin inhibitor JPM-OEt (Drug Synthesis and Chemistry Branch, Division of Cancer Treatment and Diagnosis, National Cancer Institute, MD) reconstituted in dimethyl sulfoxide (DMSO), or DMSO as control, this was refreshed every 48 hours.

Microscopy

Bright-field images at 40× magnification were taken on the Olympus BX41 using a DP25 camera and DP2-BSW software (Olympus, TYO, Japan) to observe overall multicellular morphology. Nuclei were labelled with cell permeable Hoechst (Thermo Scientific, MA, USA, 33342) and rinsed with PBS. Confocal microscopy was performed on a Zeiss LSM 780 inverted confocal microscope (Zeiss, Thornwood, NY, USA) with a 10×/0.45 air-objective, with 37° C., 5% $CO_2$ incubation. Z-stacks were captured using ZEN software (Zeiss) and 3D-reconstructions were created using IMARIS (Bitplane, Switzerland) including volume rendering.

Quantification of 3D Cultures

Images of 3D cultures were processed and analyzed using the Fiji distribution of IMAGEJ (Schindelin et al. 2012) as follows. Extraction and mask generation of the individual cultures was carried out by applying an edge filter followed by an unsharp mask (radius=6, mask=0.8). The resulting image was blurred using a Gaussian filter (sigma=4) to make subsequent thresholding more accurate. A threshold was applied, manually adjusted if required and used to create a binary mask. The resulting mask was filtered by size to remove small, erroneous, debris. Each individual 3D cultures mask was then measured for its perimeter and convex hull lengths. The result for the convex hull length was divided by the perimeter length to generate the convex hull to perimeter ratio used for the subsequent data analysis.

All statistics were calculated and graphed using PRISM version 7. Frequency distributions for each sample group (n=3) were generated to show the distribution of convex hull to perimeter ratios for each sample group. Each distribution was then fitted with a Log Gaussian fit and the centers of each fit were compared for statistical variation. Variation in mean convex hull to perimeter ratio was determined using one-way ANOVA followed by Tukey's post hoc analysis.

Protease Labelling and Western Blotting

Cells were lysed by freezing in citrate buffer (50 mM citrate, pH 5.5, 0.5% CHAPS, 0.1% TRITON™ X-100, 4 mM DTT). For cathepsin B activity gels, activity-based probes [GB123 (1 µM) (29) or BMV109 (0.1 µM) (Verdoes et al. 2013)] were added to lysates from a 100×stock, and proteins were incubated for 30 minutes at 37° C. The addition of 4×sample buffer (40% glycerol, 200 mM Tris-HCl pH 6.8, 0.04% bromophenol blue, 5% beta-mercaptoethanol) stopped the reaction with boiling for 10 minutes. Proteins (30-50 µg) were separated by SDS-PAGE (on either 15% acrylamide or gradient 4-20% gels, precast from BIO-RAD, CA, USA) and visualized using a TYPHOON flatbed laser scanner (GE Healthcare, UK) for Cy5 fluorescence. For immunoblotting, proteins were transferred to nitrocellulose membranes and subjected to standard Western blotting protocols. Membranes were incubated with 1 µg/ml primary antibodies against stefin A, cathepsin B (R&D Systems, Minneapolis, USA, AF965), DSG3 (Life Technologies, 326300), E-cadherin (Novus, NB-110-56937), or 1:10,000 dilutions of β-actin (Sigma-Aldrich, MO, USA, A22280) or GAPDH (Cell Signaling Technology, MA, USA, 8884). Signal was detected using ECL (GE Healthcare), G:Box GelDoc (Syngene, CBG, UK) and GeneSys (Syngene) software with automatic exposure.

Collection of Secreted Proteins

To collect secreted proteins, cells were incubated in serum free media for 24 hours. Floating cells were removed by centrifugation (twice) and conditioned media was concentrated using 3 KDa centrifugal filters (Millipore, MA, USA), and western blotting protocol was followed as described above.

SRB Proliferation Assay

An SRB proliferation assay was conducted as previously described (Vichai and Kirtikara, 2006) with the N1ME wild type and stefin A low clones over 7 days, with a starting cell number of 3,000 cells.

Mass Spectrometry

Sample Preparation for Mass Spectrometry

Purified plasma membrane proteins were prepared from N1ME wild type and N1ME stefin A low cells (50 µg protein, n=3) using a modified carbonate extraction method (Fujiki, 1982). All steps were carried out at 4 C to minimize protease degradation. Briefly, >6×106 cells were washed twice in PBS and pelleted for 5 min at 300 g. Cell pellets were resuspended in 50 mM Tris/1 mM EDTA with protease inhibitors (EMD Millipore Corporation, San Diego, USA), and cells allowed to swell for 45-60 min with rotation. Swollen cells were frozen overnight, sonicated for 5 min as thawing, vortexed briefly and sonicated for a further 15 min before disruption using a 25 gauge ¾ inch needle and monitored for cell breakage using trypan blue staining. When cells were >90% lysed, nuclei and remaining intact cells were removed at 21,000 g for 15 min with the supernatant collected and incubated with an equal volume of ice cold 0.2 M sodium carbonate (pH 11) for 60 min rotating at 4 C. To sediment membranes, the supernatant was spun at 107,000 g for 60 min. The membrane protein pellet was resuspended and washed in 0.1 M sodium carbonate and the pellet was collected at 107,000 g for 30 min. The membrane protein pellet was resuspended in 50 µl of urea. Adequate amount of sample (6 µL) was used for BCA (Thermo Scientific, IL, USA) protein quantification. The supernatant after membrane sedimentation was collected and precipitated with acetone over night as the soluble protein fraction.

Protein Digestion and De-salting

After protein quantification, 50 µg of protein was taken from each sample and made up to a total volume of 100 µL in 7 M urea/2 M thiourea/50 mM Tris in 0.1% Rapigest (Waters, Milford, MA). Proteins were reduced with 2 mM tri(2-carboxyethyl)phosphine hydrochloride (Sigma-Aldrich, C4706) at 28 C for at least 4 hour on a shaker and alkylated with 25 mM iodoacetamide (Sigma-Aldrich) for 30 min at 21 C in the dark. Proteins were then digested for 18 hour at 37 C in a 1:50 w/w trypsin/protein ratio (Promega, V5111). After digestion, samples were reduced to half the volume using a SpeedVac. The samples were de-salted and cleaned using Sep-Park cartridges (Water, Milford, MA). Peptides were eluted from the cartridge with 85% acetonitrile and 0.5% trifluoroacetic acid (TFA) and vacuum concentrated, with peptides reconstituted in 5% acetonitrile and 0.5% TFA.

Proteomic Analysis

Proteomic experiments were performed in biological triplicate, with technical replicates (n=2), with MIAPE-compliance (Gopal, 2015 & Greening, 2016). A nanoflow UPLC instrument (Ultimate 3000 RSLCnano, Thermo Fisher Scientific) was coupled online to an Q-Exactive HF Orbitrap mass spectrometer (Thermo Fisher Scientific) with a nanoelectrospray ion source (Thermo Fisher Scientific). Peptides were loaded (Acclaim epMap100, 5 mm×300 µm i.d., µ-Precolumn packed with 5 µm C18 beads, Thermo Fisher Scientific) and separated (BioSphere C18 1.9 µm 120 Å, 360/75 μm×400 mm, NanoSeparations) with a 120-min linear gradient from 0-100% (v/v) phase B (0.1% (v/v) FA in 80% (v/v) ACN) at a flow rate of 250 nL/min operated at 55° C. The mass spectrometer was operated in data-dependent mode where the top 10 most abundant precursor ions in the survey scan (350-1500 Th) were selected for MS/MS fragmentation. Survey scans were acquired at a resolution of 60,000, with MS/MS resolution of 15,000. Unassigned precursor ion charge states and singly charged species were rejected, and peptide match disabled. The isolation window was set to 1.4 Th and selected precursors fragmented by HCD with normalized collision energies of 25 with a maximum ion injection time of 110 msec. Ion target values were set to 3e6 and 1e5 for survey and MS/MS scans, respectively. Dynamic exclusion was activated for 30 sec. Data was acquired using Xcalibur software v4.0 (Thermo Fisher Scientific).

Database Searching and Protein Identification

Raw data were pre-processed as described (10) and processed using Proteome Discoverer (v2.1, Thermo Fisher Scientific). MS2 spectra were searched with Mascot (v2.1, Matrix Science, UK), Sequest HT (v2.1, Thermo Fisher Scientific), and MS-Amanda (v2.1, Research Institute of Molecular Pathology, Austria) against a database of 133,798 ORFs (UniProtHuman, July 2016). Peptide lists were generated from a tryptic digestion with up to two missed cleavages, carbamidomethylation of cysteines as fixed modifications, and oxidation of methionines and protein Nterminal acetylation as variable modifications. Precursor mass tolerance was 10 ppm, product ions were searched at 0.02 Da tolerances, minimum peptide length defined at 6, maximum peptide length 144, and max delta CN 0.05. Peptide spectral matches (PSM) were validated using Percolator based on q-values at a 1% false discovery rate (FDR) (Greening, 2013 & Brosch, 2009). With Proteome Discoverer, peptide identifications were grouped into proteins according to the law of parsimony and filtered to 1% FDR (Nesvizhskii, 2005). Scaffold Q+S (Proteome Software Inc., OR, v4.5.3) was employed to validate MS/MS-based peptide and protein identifications from database searching. Initial peptide identifications were accepted if they could be established at greater than 95% probability (PEP 5%) as specified by the Peptide Prophet algorithm (Keller, 2002). Protein probabilities were assigned by the Protein Prophet algorithm (Nesvizhskii, 2005). Protein identifications were accepted with 1% FDR and contained at least 2 identified unique peptides. These identification criteria typically established <1% false discovery rate based on a decoy database search strategy at the protein level. Proteins that contained similar peptides and could not be differentiated based on MS/MS analysis alone, were grouped to satisfy the principles of parsimony. Contaminants, and reverse identification were excluded from further data analysis. Data normalization based on identified spectral counts was performed in Scaffold. For gene ontology enrichment and network analyses, UniProt (www.uniprot.org), KEGG (http://www.genome.jp/kegg/pathway.html), and DAVID (http://david.abcc.ncifcrf.gov/) resources were utilized. Clustering of samples was performed by principal component analysis (PCA) and visualized using ggplot2 (Wickham, 2009) and ggfortify (https://cran.rproject.org/web/packages/ggfortify/index.html).

Stefin A In Vitro Inhibition of Cathepsin B

To determine if stefin A can inhibit cathepsin B, X and L in vitro, N1ME cells were lysed according to the previous protocol. Increasing concentrations of recombinant stefin A (R&D Systems, 1407-PI-050) were incubated with the lysate for 15 min at 37 C, followed by incubation with BMV109 for 15 min at 37 C. Samples were then separated on a gel and imaged as previously described.

Densitometry Analysis

Using the Fiji distribution of ImageJ (Schindelin et al., 2012), densitometric analysis was performed by taking the background-subtracted density of each band and normalizing to loading control. This was then graphically represented. If appropriate, the density was standardized to N1ME wild type protein density levels, averaged and shown as a ratio.

Cleavage Assay

To determine if proteins could be cleaved by cathepsin B, 0.2 μg of recombinant cathepsin B was incubated with 1 μg of recombinant DSG3 (R&D Systems) for 3 or 16 hours at 37° C. The ABP GB123 probe was added to a control sample to ensure cathepsin B was active. To stop the reaction, 4× sample buffer was added to the samples, boiled at 95° C. for 10 min and run on an SDS-PAGE gel and imaged as previously described. Following imaging, the gel was stained overnight with COOMASSIE Blue (BIO-RAD), then destained with destain buffer (Bio-Rad) until appropriate contrast of bands was visible, and imaged.

Immunofluorescence

Cells were plated into an 8 well coverslip-based chamber slide (Thermo Scientific, NUN155409) and allowed to adhere overnight. Following fixing, permeabilization and blocking (details in supplementary material), cells were incubated with DSG3 primary antibody overnight at 4° C. Fluorescently-conjugated secondary antibodies were used to detect primary antibody binding and nuclei was stained with DAPI (Sigma-Aldrich, 10236276001). Fluorescence was detected using a ZEISS LSM 780 inverted confocal microscope (Zeiss, Thornwood, NY, USA) and Zen software.

Mouse Models

Mouse investigations were performed after approval by the La Trobe University Animal Ethics Committee. Bl/6 MMTV-PyMT positive female mice were injected (intraperitoneal, 200 μl/20 g mouse) daily with 50 mg/kg CA-074 or vehicle (5% DMSO/saline) from day 30-49. On day 50, mice were culled and second, third and fourth mammary glands were resected and sent for histology. Mouse tissues were fixed in 10% buffered formalin for 6 hours and paraffin-embedded. Sections at three different depths throughout the mammary gland were taken and were stained with hematoxylin and eosin according to standard protocols. Alternatively, sections were stained with 1 μg/ml anti-α-smooth muscle actin (ABCAM, ab66133) or with isotype control antibodies, as above. Sections were scored by a pathologist blinded to treatment groups (Sandra O'Toole) for the presence of invasive regions of cancer growth within the mammary gland. Experiment included 8 mice per group.

Statistical Analysis

Statistics were conducted using the data analysis software package within GRAPHPAD PRISM v7 for WINDOWS (GRAPHPAD Software) and PASW Statistics 18 (SPSS). Error bars indicate SEM unless otherwise stated.

Results

Figure 2:
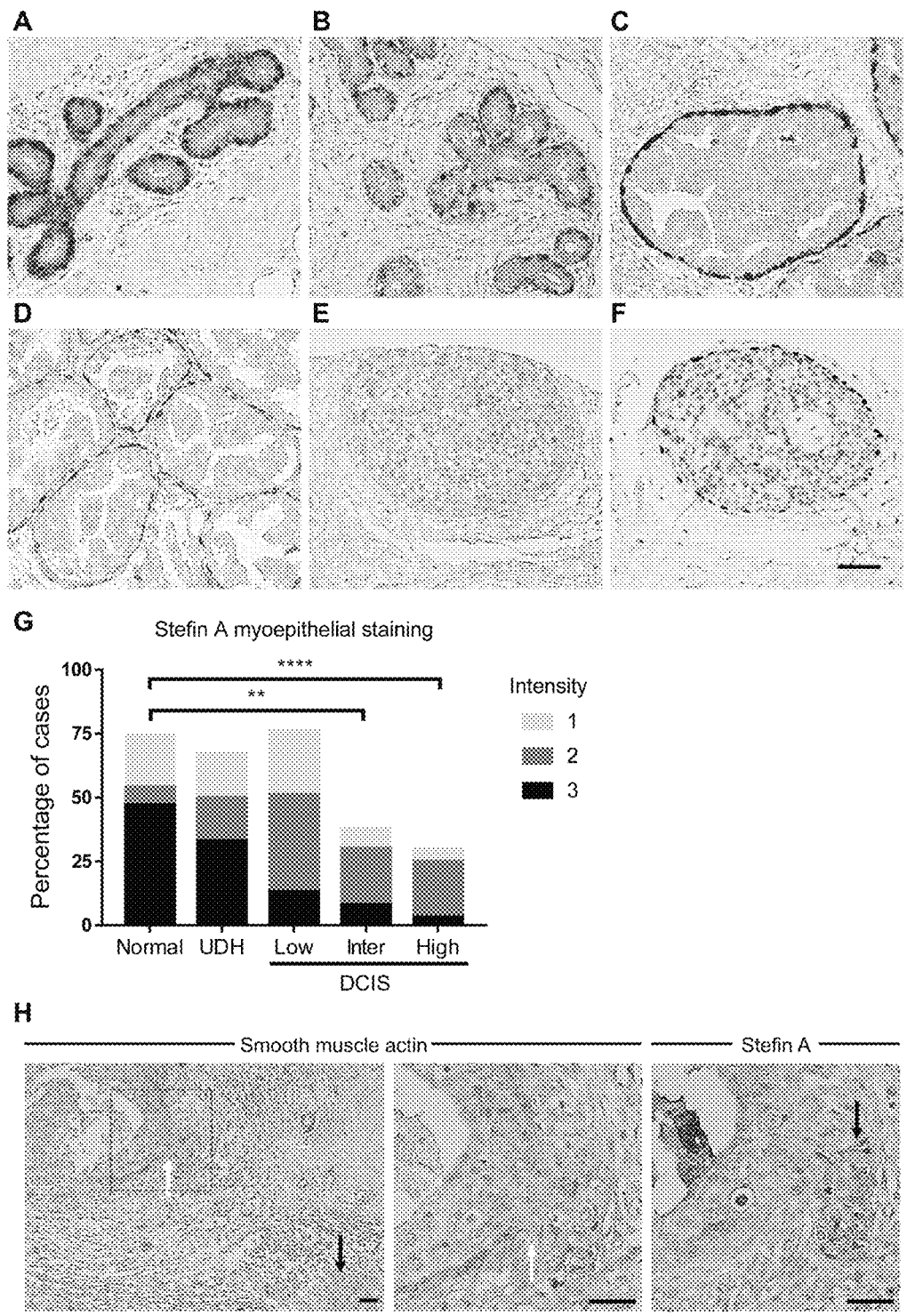
FIG. 2 Stefin A expression in human normal and carcinoma tissue. Sections of formalin-fixed, paraffin-embedded tissue were stained with rabbit anti-human stefin A and visualized with DAB (brown). All sections were counterstained with hematoxylin (blue nuclei). Expression of stefin A in myoepithelial cells surrounding (A, B) normal breast ducts and (C) DCIS lesions. (D) Aberrant or (E) no myoepithelial stefin A expression in DCIS lesions. (F) Mouse anti-human p63 was used as a positive control for the presence of myoepithelial cells in all tissues. (G) Myoepithelial stefin A expression was pathologist scored and compared between groups: normal, usual ductal hyperplasia (UDH), DCIS grades low, intermediate (inter) and high. The percentage of the scoring intensity is shown. Comparison is by Chi-square test on patient numbers in each group **$p<0.0001$, $p<0.01$. n=138 patients. (H) Stefin A expression is lost in micro-invasive regions. DCIS tissue with identified micro-invasive regions were stained with rabbit anti-human stefin A and smooth muscle actin (SMA) and visualized with DAB (brown). All sections were counterstained with hematoxylin. The presence of myoepithelial cells was confirmed by SMA positivity on serial sections. White arrows indicate the focal break in the myoepithelial boundary. Black arrows indicate invasive cells. Scale bars represent 50 μm.

Stefin a Expression is Absent in Myoepithelial Cells Surrounding High Grade DCIS Lesions To characterize cell-specific stefin A expression during the early stages of breast tumor development, a tissue microarray (TMA) encompassing sections of >800 lesions were stained with antibodies specific for stefin A. These lesions ranged from benign ducts, including usual ductal hyperplasia, up to DCIS of low, intermediate or high nuclear grade from 138 patients diagnosed with DCIS only. Expression patterns were confirmed by the use of two independent stefin A antibodies (FIG. 1A). Stefin A was typically expressed in the myoepithelial cells surrounding normal ducts (FIG. 2A and B). This myoepithelial expression was retained in hyperplastic and low grade DCIS lesions (FIG. 2C and D), yet was reduced or absent in many intermediate and high grade DCIS lesions (FIG. 2E). The distinction between DCIS and IDC is the presence of the myoepithelial cell layer (Polyak, 2005) and myoepithelial marker immunohistochemistry (IHC) is used widely in diagnostic clinical practice. To rule out loss or attenuation of the myoepithelial layer in stefin A muscle actin (SMA), a cytoplasmic/cytoskeletal myoepithelial marker, was also used to highlight the presence or absence of the myoepithelial cells, including identification of any small focal breaks in the myoepithelial cell boundary (FIG. 2H, white arrows). In line with an association between stefin A loss and tumor invasion, it was observed that DCIS lesions with micro-invasion did not express myoepithelial stefin A. These results supported the association of the loss of myoepithelial expression of stefin A and increased risk of invasion suggested by the TMA study.

TABLE 1

Tissue microarray stefin A correlation data. Correlation of myoepithelial and epithelial stefin A expression with DCIS grade, ER status, histological grade and DCIS size. n = 138 patients.

| | | | Myoepithelial stefin A expression | | | | | Epithelial stefin A expression | | | | |
|---|---|---|---|---|---|---|---|---|---|---|---|---|
| | | Total | H-score | | | | Total | H-score | | | | |
| | | patients | 0 | 1-99 | 100-199 | 200-300 | p-value | patients | 0 | 1-99 | 100-199 | 200-300 | p-value |
| DCIS grade* | Normal (A) | 17 | 7 | 5 | 2 | 3 | 0.005* | 9 | 3 | 4 | 1 | 1 | 0.041* |
| | UDH(A) | 6 | 1 | 4 | 0 | 1 | | N/A | N/A | N/A | N/A | N/A | |
| | DCIS Low (A) | 8 | 3 | 5 | 0 | 0 | | 43 | 28 | 11 | 4 | 0 | |
| | DCIS intermediate (A) | 44 | 28 | 13 | 2 | 1 | | 8 | 4 | 4 | 0 | 0 | |
| | DCIS High (A) | 63 | 43 | 19 | 1 | 0 | | 64 | 21 | 34 | 3 | 6 | |
| ER status | Negative | 7 | 4 | 2 | 1 | N/A | 0.137 | 7 | 3 | 4 | 0 | 0 | 0.808 |
| | Positive | 26 | 15 | 11 | 0 | N/A | | 27 | 12 | 12 | 1 | 2 | |
| PR status | Negative | 8 | 5 | 2 | 1 | N/A | 0.155 | 8 | 3 | 5 | 0 | 0 | 0.669 |
| | Positive | 25 | 14 | 11 | 0 | N/A | | 26 | 12 | 11 | 1 | 2 | |
| Histological grade | 1 | 7 | 2 | 5 | 0 | N/A | 0.121 | 7 | 3 | 3 | 1 | 0 | 0.138 |
| | 2 | 8 | 5 | 2 | 1 | N/A | | 8 | 3 | 4 | 0 | 1 | |
| | 3 | 7 | 6 | 1 | 0 | N/A | | 8 | 0 | 8 | 0 | 0 | |
| DCIS size | <20 mm | 15 | 9 | 5 | 1 | N/A | 0.806 | 16 | 4 | 10 | 1 | 1 | 0.832 |
| | >20 mm | 6 | 4 | 2 | 0 | N/A | | 6 | 2 | 4 | 0 | 0 | | negative lesions, serial sections were stained with p63 (FIG. 2F), a nuclear myoepithelial marker. Only p63 positive samples were included in the analysis.

Comparison of stefin A staining intensity on p63-positive normal, hyperplasia and DCIS lesions revealed that patients with intermediate and high grade DCIS had significantly lower myoepithelial expression of stefin A (FIG. 2G). Stefin A expression inversely correlated with DCIS grade, but did not correlate with ER, PR, histological grade or tumor size (Table 1).

The negative correlation between stefin A expression and DCIS grade was restricted to myoepithelial cells. Evaluation of stefin A expression in the tumor epithelium (FIG. 1B) revealed an increase in DCIS lesions in general, and an increase with grade (FIG. 1C., Table 1). This suggests that the role of stefin A in early tumorigenesis is likely cell dependent and therefore it is the loss of myoepithelial cell stefin A surrounding DCIS lesions that is of interest for this study.

Figure 3:
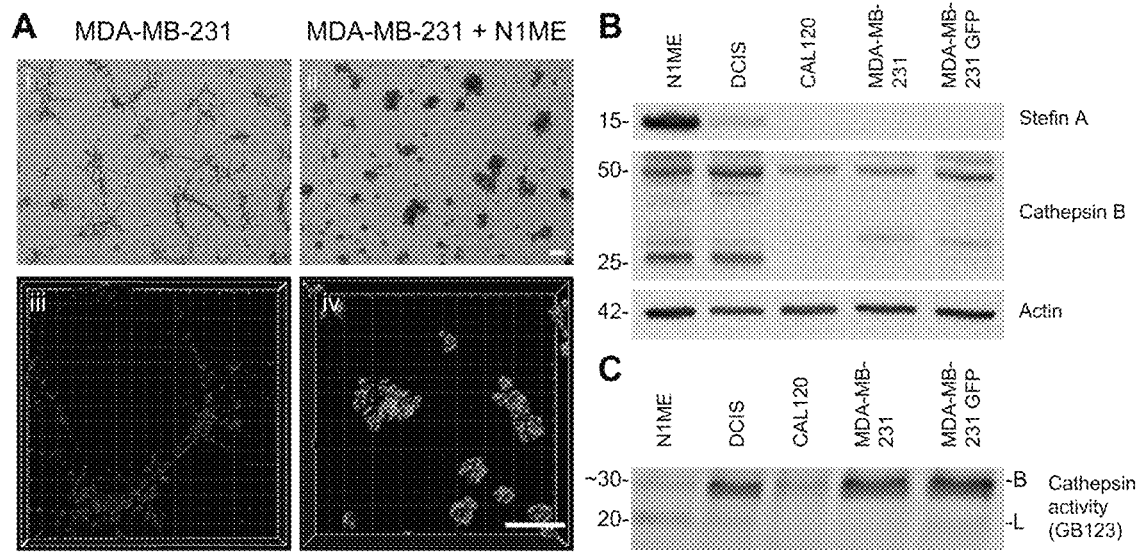
FIG. 3 Development and characterization of a 3D culture model. (A)(i) 3D culture of MDA-MB-231 breast cancer cell line grown on reconstituted basement membrane. (ii) 3D co-culture of MDA-MB-231 cells with N1ME cherry-labelled myoepithelial cells. (iii) Confocal images, rendered in IMARIS, of MDA-MB-231 Hoechst stained cells (blue) alone and (iv) co-cultured with myoepithelial cells (red). Scale bars represent 200 μm. (B) Expression of stefin A and cathepsin B detected by Western blotting in whole cell lysates. The 28 and 30 kDa bands reflect mature cathepsin B. β-actin was used as a loading control. (C) Cathepsin B and L activity were determined by the use of an activity based probe (GB123). Blots representative of 3 independent experiments.
Figure 4:
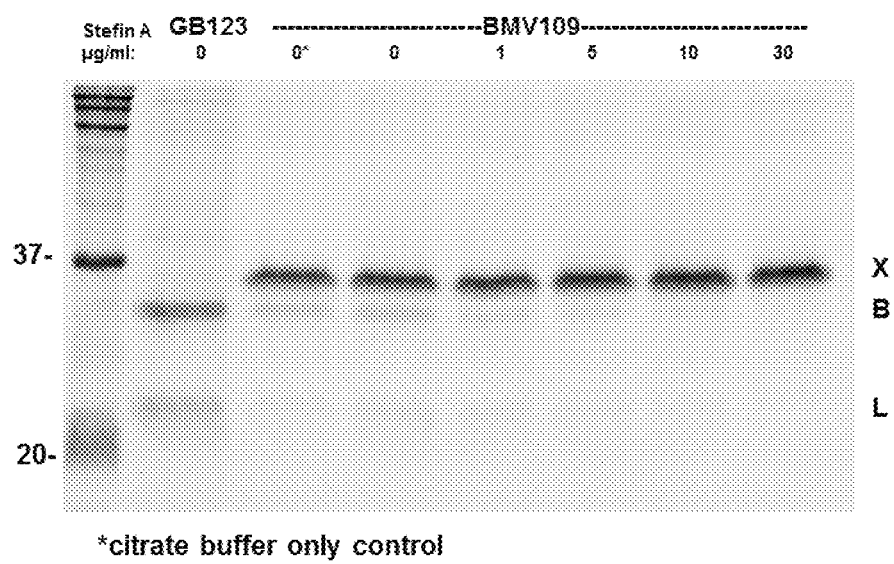
FIG. 4 Stefin A inhibition of cathepsin B. SDS-PAGE gel electrophoresis of N1ME cell lysate incubated with increasing concentrations of recombinant stefin A. Cathepsin activity was measured by the use of the BMV109 activity based probe, GB123 was used as control to confirm cathepsin B and L bands.

Patients with high grade DCIS lesions have an increased risk of local invasion compared to low grade lesions (Wood, 2008). However, as clinical follow-up on the subsequent development of invasive carcinoma (fortunately a rare event as patients received modern treatment) was not available, we investigated stefin A expression in high grade DCIS lesions with associated micro-invasive regions, the earliest phase of invasion. Micro-invasion is defined as an invasive focus measuring no more than 1 mm. The cases studied had previously diagnostically confirmed absence of a myoepithelial cell layer by the use of p63 and smooth muscle myosin heavy chain expression. In this study alpha smooth Development of a 3D Model to Test the Function of Myoepithelial Stefin A in Invasion We developed a 3D model of DCIS in vitro whereby the immortalized human myoepithelial cell line (N1ME, hTERT immortalized by K. Polyak) was co-cultured with invasive breast cancer cell lines on a reconstituted basement membrane (CULTREX®). As expected, the invasive breast cancer cell line MDA-MB-231 grew rapidly and invasively in 3D (FIG. 3A). However, when co-cultured with N1ME myoepithelial cells at a 1:1 ratio, the MDA-MB-231 cells were reverted to a DCIS-like spheroid structure that lacked invasive protrusions (FIG. 3A). We confirmed that these N1ME myoepithelial cells were indeed positive for stefin A expression by Western blot. In accordance with the immunohistochemistry data, the N1ME line had the highest expression of stefin A compared to a panel of human breast cancer cell lines (FIG. 3B). Cathepsin B, a cysteine protease and target of stefin A, was expressed by all cell lines (FIG. 3B). To determine the proportion of active cathepsin B and L, the activity-based probe GB123 was used (Blum, 2007). Despite having high cathepsin B expression, the N1ME cells had very low cathepsin B activity (FIG. 3C), most likely due to inhibition by stefin A. In fact, we demonstrated that cathepsin B and L from myoepithelial cells can be inhibited by stefin A in vitro (FIG. 4). Cathepsin B activity was increased in the cell lines with highest metastatic potential (MDA-MB-231), as expected in view of its pro-tumorigenic roles (FIG. 3C). In contrast, although cathepsin L was detected in myoepithelial cells, its activity throughout the cell lines did not inversely correlate with stefin A expression.

Together, these data suggest that stefin A expression inversely correlates with cathepsin B activity in these cell lines.

Reduction of Stefin A Promotes Breast Cancer Cell Invasion

Figure 5:
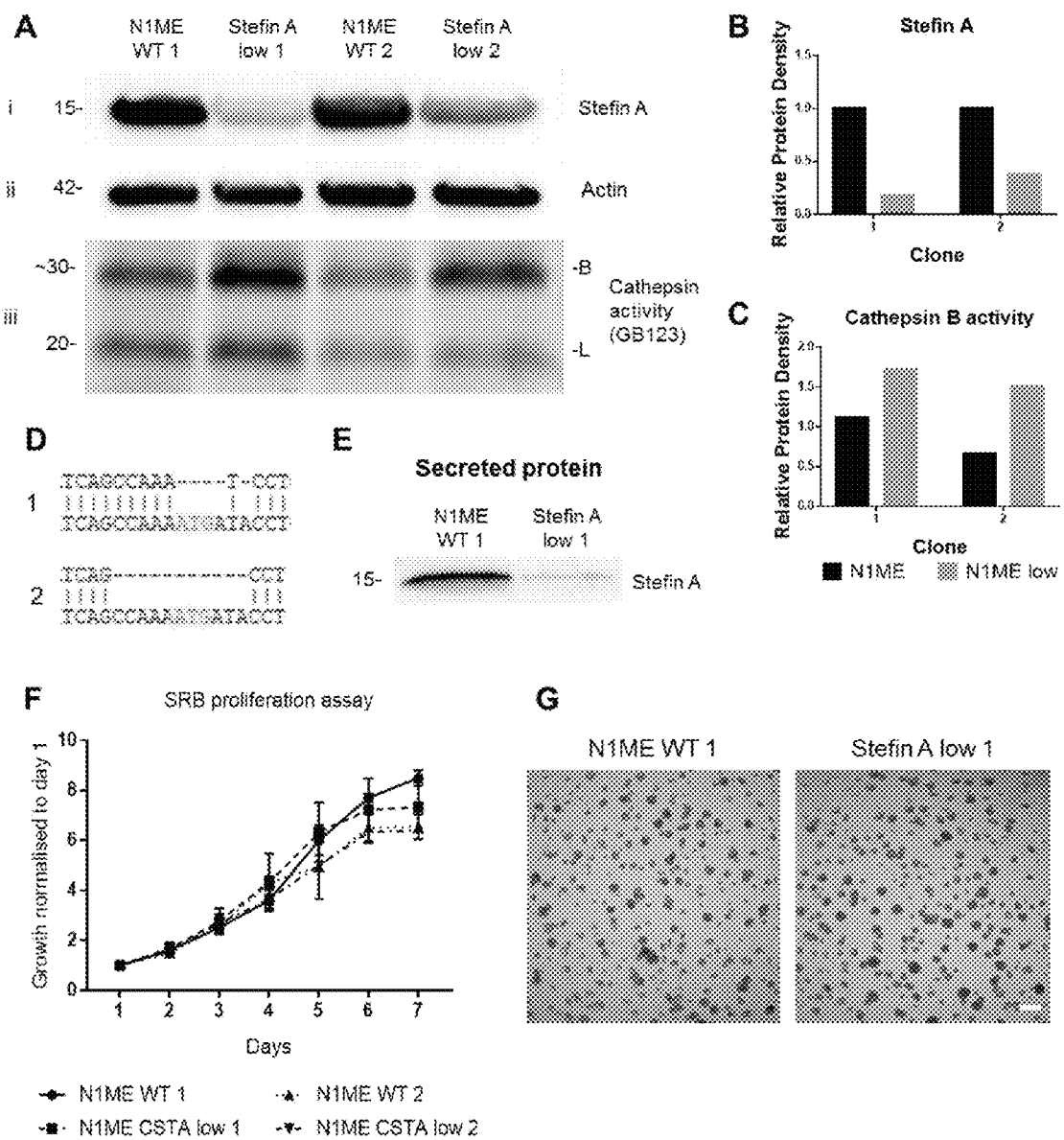
FIG. 5 Generation of myoepithelial stefin A low cell lines. Gene-editing with transcription activator-like effector nucleases (TALENs) was used to generate two cell lines with heterozygous deletions ablating the start codon of the gene encoding stefin A. (Ai) There was a decrease in stefin A protein levels in stefin A low N1ME cells compared to wild type cells. (Aii) Actin expression is shown as loading control. (Aiii) Cathepsin B activity, determined by the use of the GB123 activity based probe, demonstrated an increase in activity in the stefin A low clones in comparison to their wild type clones. Densitometry analysis was conducted using ImageJ in comparison to loading control (actin) to confirm (B) a 60-80% decrease in stefin A protein levels, and (C) an increase in cathepsin B activity levels in the stefin A low myoepithelial cells compared to wild type. (D) Stefin A low clones were sequenced to determine the TALEN induced mutation (5 out of 8 sequencing reads yielded the deletion shown in panel D). (E) Conditioned media from the stefin A low clone 1 revealed less stefin A was secreted compared to N1ME wild type. (F) An SRB proliferation assay was conducted to demonstrate non-statistical differences in growth between the wild type clones and their stefin A low clone. Data are represented as mean±SEM. (G) Growth of the N1ME wild type and N1ME stefin A low clone in 3D revealed no differences in growth. Scale bar represents 200 μm.

To determine whether myoepithelial cell stefin A is critical for suppression of breast cancer cell invasion in 3D, a stefin A low (heterozygote null) myoepithelial line was created using transcription activator-like effector nucleases (TALENs) (FIG. 5). TALEN-knockout of one allele of Stefin A in myoepithelial cells blocked the ability of the myoepithelial cells to prevent invasion of MDA-MB-231 cells.

Figure 6:
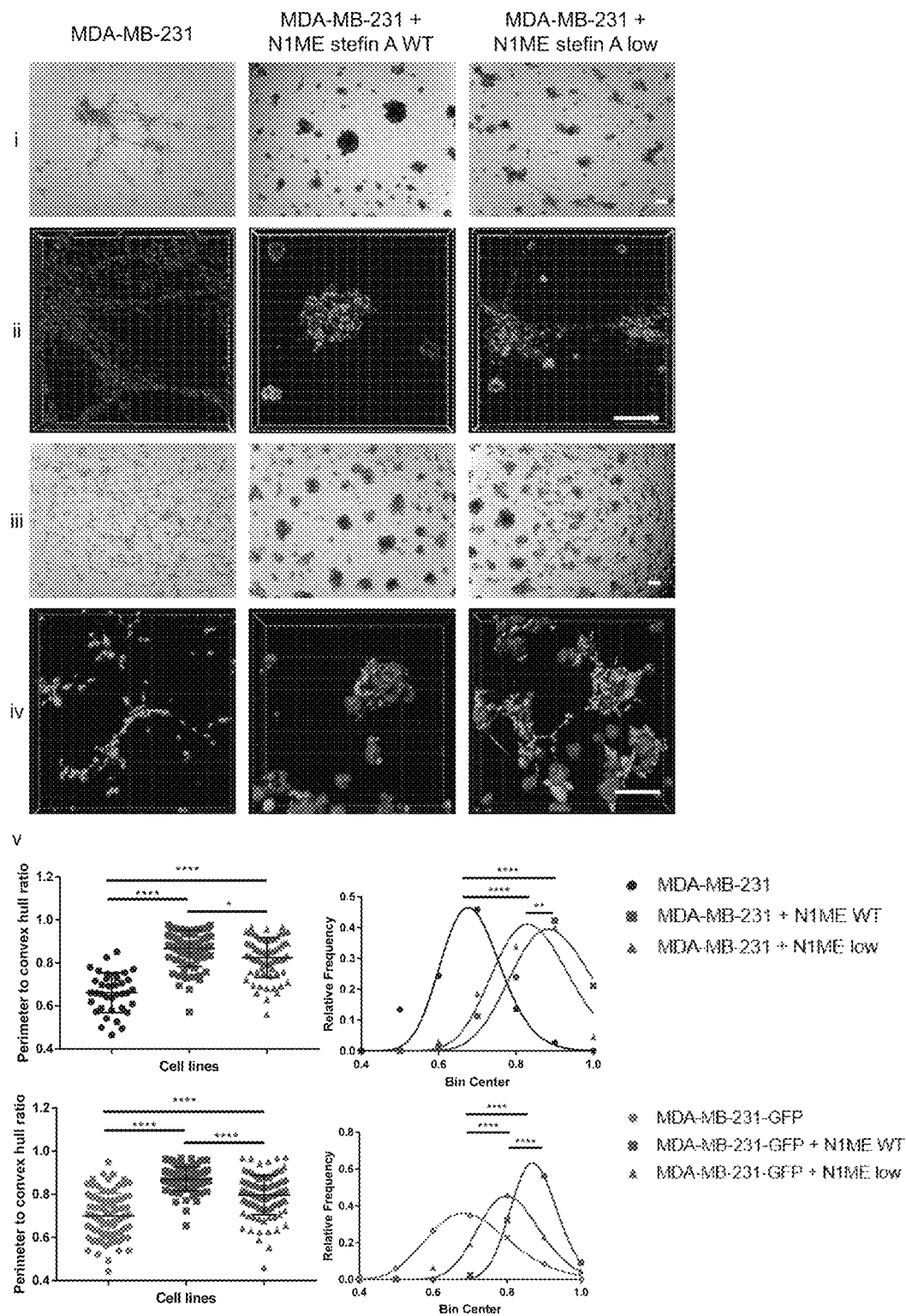
FIG. 6 Decreased myoepithelial stefin A expression promotes MDA-MB-231 invasion in 3D co-culture. MDA-MB-231 cells cultured alone, co-cultured with N1ME stefin A wild type, or N1ME stefin A low cells. (i) Bright field images of MDA-MB-231 (not labelled) co-cultured with myoepithelial cells. (ii) Confocal images, rendered in IMARIS, of MDA-MB-231 Hoechst stained (blue) co-cultured with myoepithelial cells (red). (iii) Bright field images of MDA-MB-231-GFP breast cancer cells co-cultured with myoepithelial cells. (iv) Confocal images, rendered in IMARIS, of MDA-MB-231-GFP (green) co-cultured with myoepithelial cells (red). Scale bars represent 200 μm. (v) Quantification of invasive outgrowths. Invasiveness of 3D cultures was determined by calculating the ratio between the perimeter and convex hull of each colony. A value of 1 indicated a smooth object, as the value moves away from 1 towards zero the number and/or size of protrusions from the colony was increased. Frequency distribution of population data under log Gaussian fit. A bin center closer to 1 indicated a smooth colony surface. Comparison of center of each curve was statistically analyzed. *p<0.05, p<0.01, **p<0.0001. n=3.
Figure 7A:
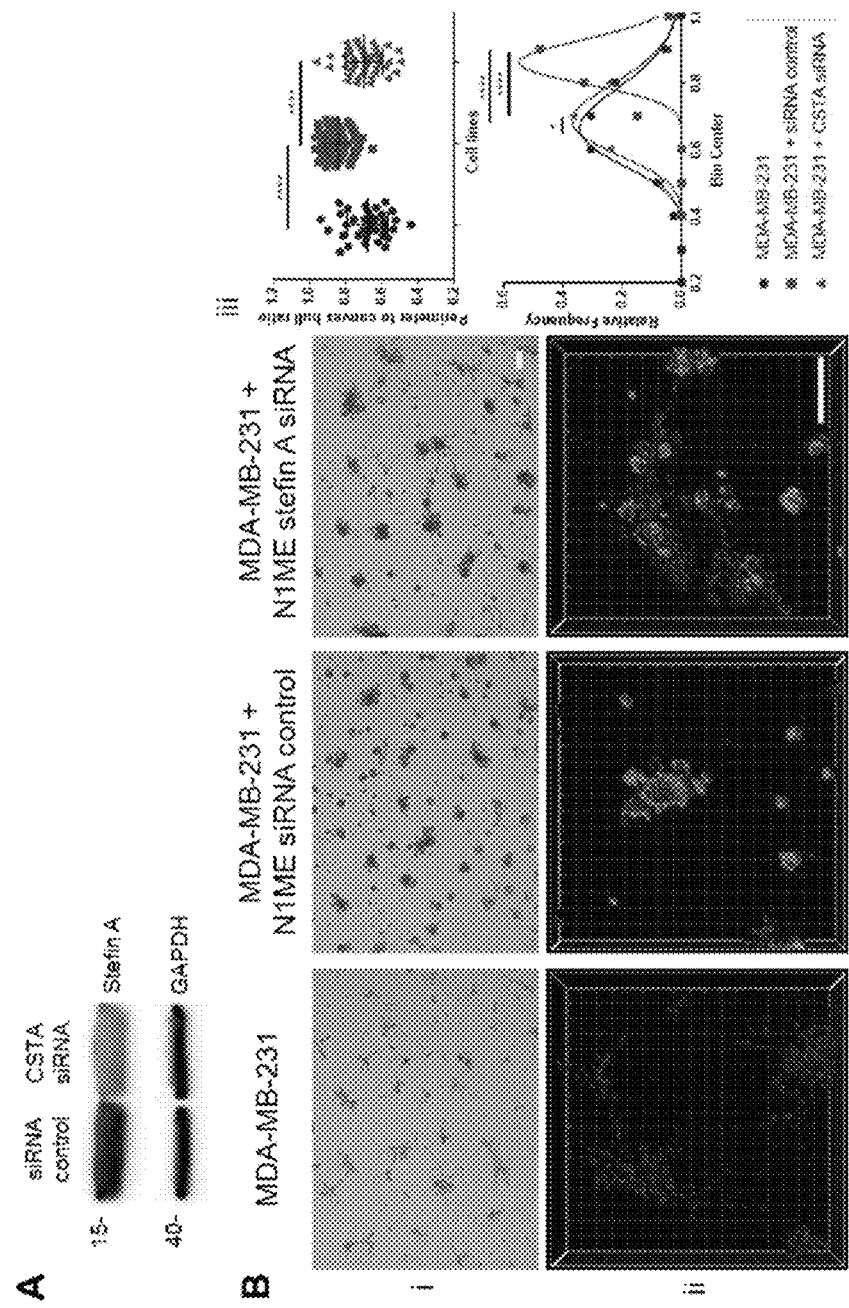
Figure 7B:
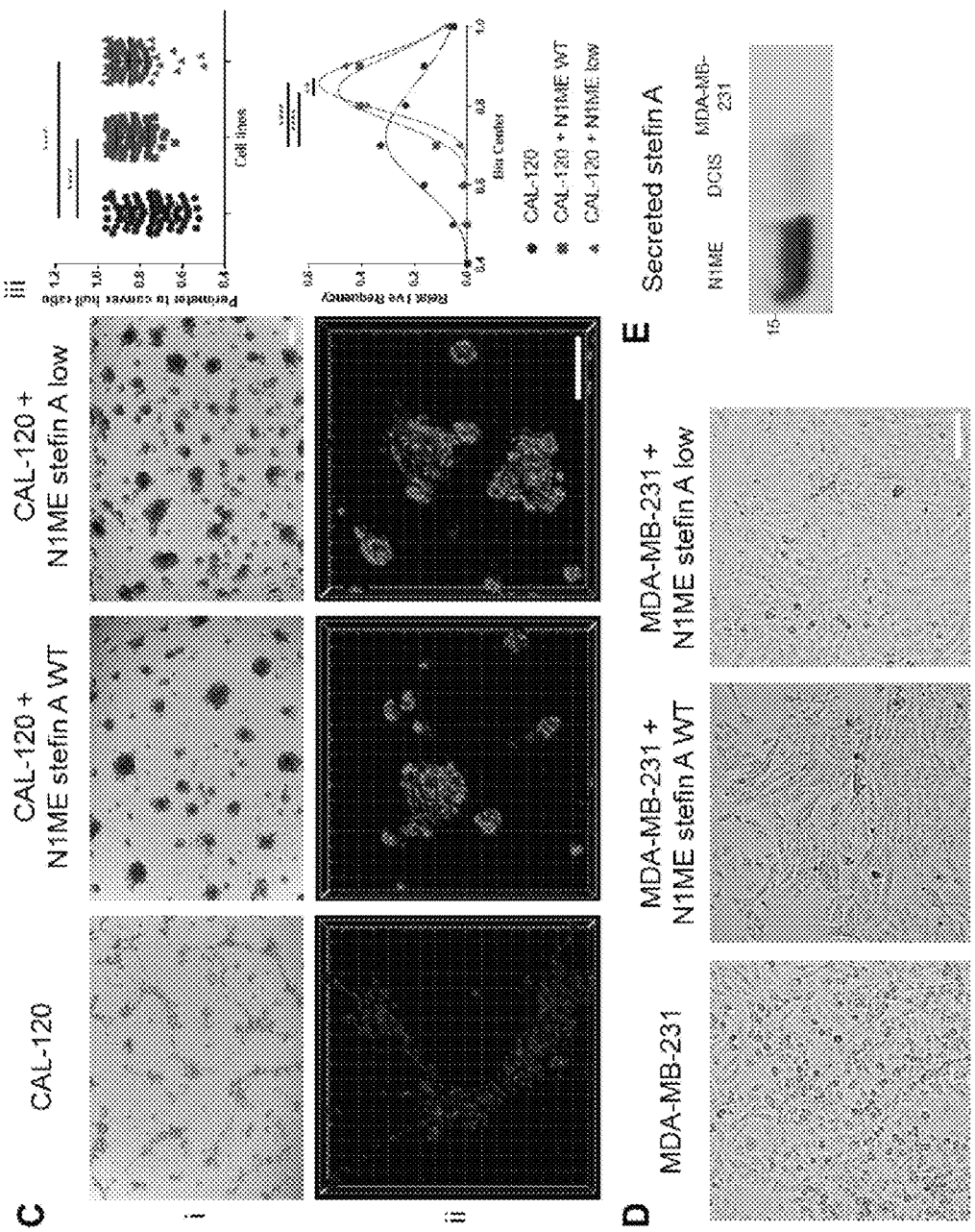

As expected, reduction in stefin A expression resulted in an increase in cathepsin B activity (FIG. 5Aiii and C). Such a correlation was not observed with cathepsin L activity. Although a reduction in stefin A expression did not impact myoepithelial cell proliferation or morphology (FIG. 5F and G), it had a dramatic effect in 3D culture. The stefin A low myoepithelial cells failed to inhibit MDA-MB-231 cell invasion to the extent observed with wild type (WT) myoepithelial cells (FIG. 6). This result suggests that a reduction in stefin A within the myoepithelial cells allows tumor cell invasion even though the myoepithelial cells remain physically present. This was observed using both unlabeled and GFP-labeled MDA-MB-231 cells (FIG. 6iii and iv). To validate these findings using an alternate gene silencing approach, stefin A expression was knocked down by siRNA (FIG. 7A and B) and the results were comparable to those seen with the gene-edited stefin A low clone. Similar results were also observed with another breast cancer cell line, CAL-120 (FIG. 7C). The impact of myoepithelial cells is specific to 3D culture, as 2D co-culture does not alter growth or morphology of MDA-MB-231 or N1ME cells (FIG. 7D). Together, these findings demonstrate the importance of stefin A in the myoepithelial-driven suppression of tumor cell invasion.

Figure 8A:
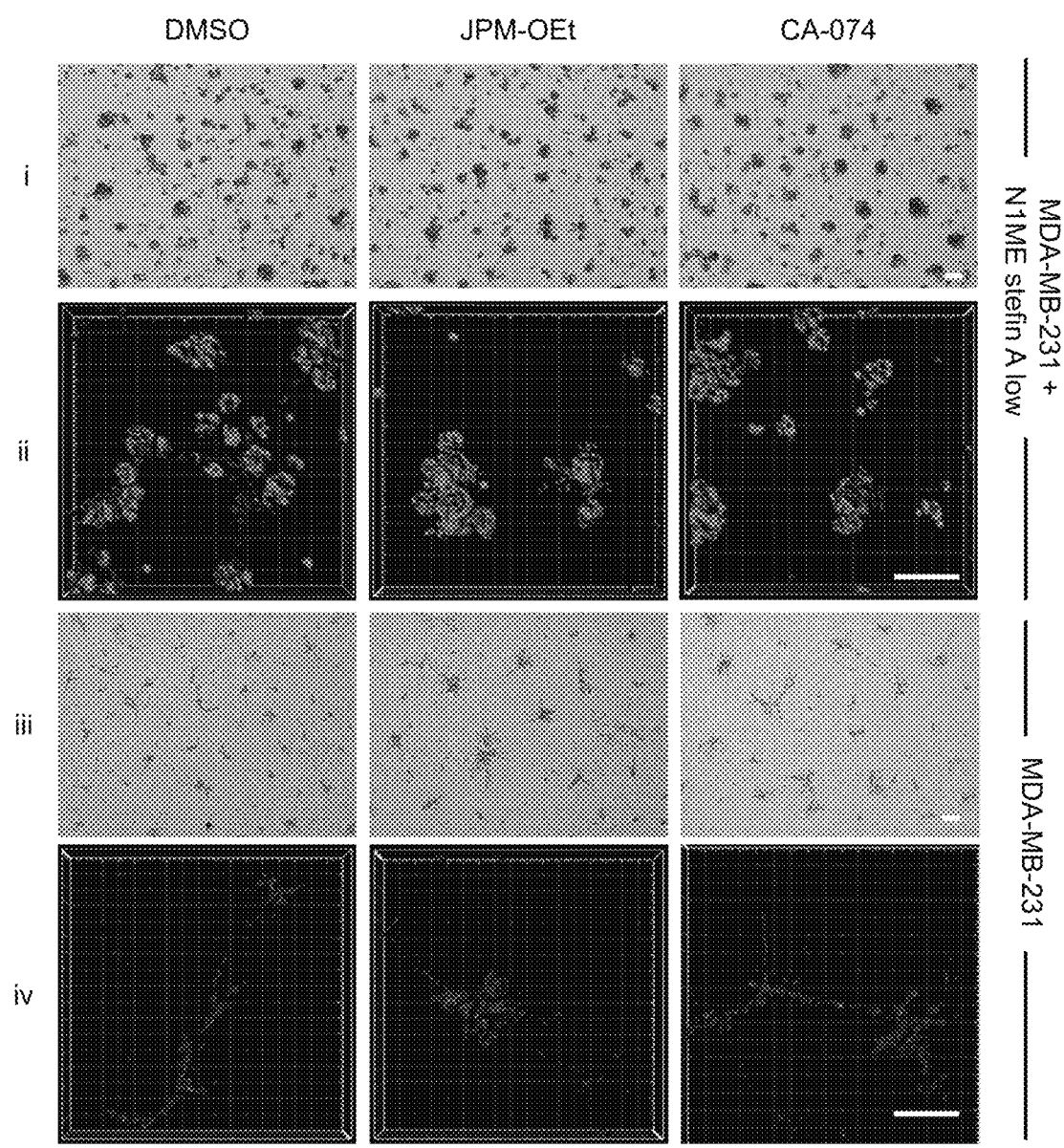
FIG. 8 Cysteine cathepsin inhibitors revert the invasive state of MDA-MB-231 cells in 3D co-culture with stefin A low myoepithelial cells. MDA-MB-231 cells alone or in 3D co-culture with N1ME stefin A low cells were treated with cysteine cathepsin inhibitors CA-074 or JPM-OEt, or DMSO control. Inhibitors were replenished every 48 hours. (i and iii) Bright field images and (ii and iv) confocal images, rendered in Imaris, of MDA-MB-231 cells (blue, Hoechst stain) alone or co-cultured with stefin A low myoepithelial cells (red). Scale bars represent 200 μm. (v) Quantification of invasive outgrowths as described in FIG. 6. NS=not significant, *p<0.05, p<0.01, **p<0.0001. n=3.
Figure 8B:
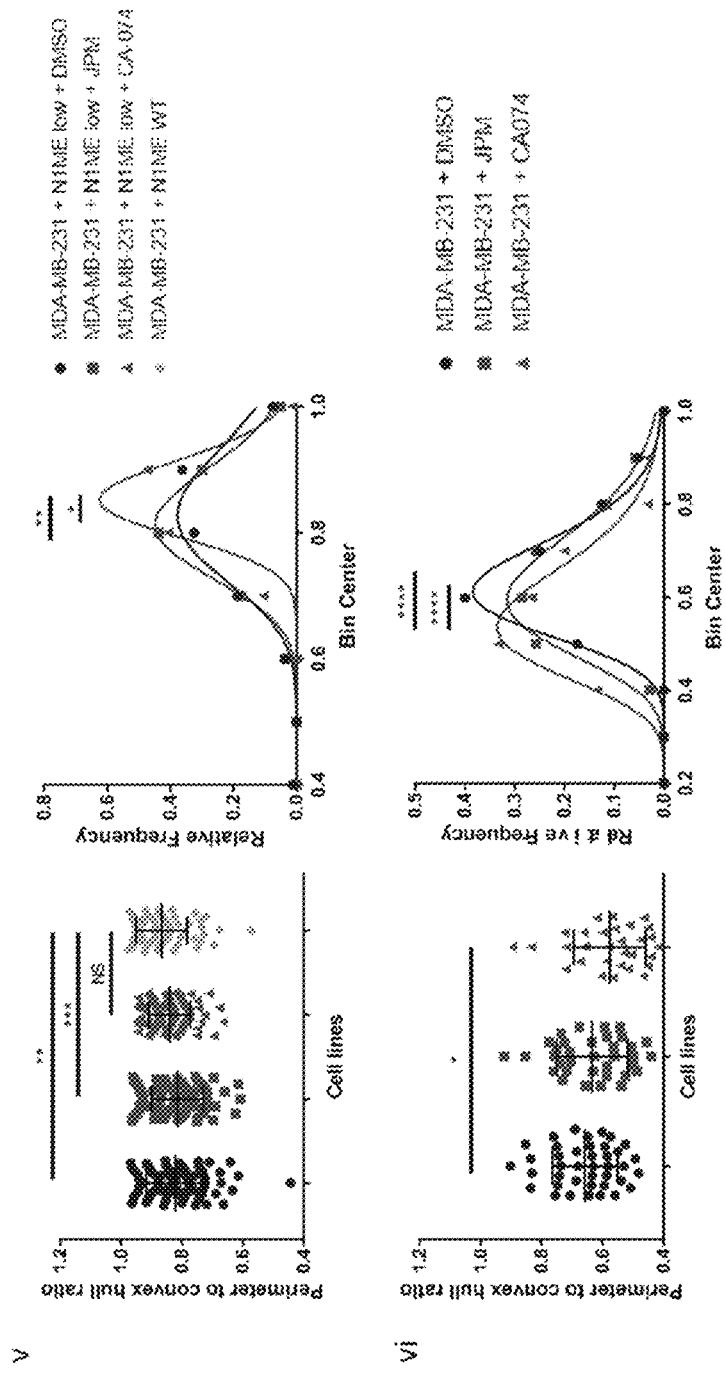

To confirm that the alteration in phenotype was due to the role of stefin A as a cathepsin inhibitor, we treated MDA-MB-231 cells alone, or co-cultured with the stefin A low myoepithelial line with cathepsin B specific (CA-074) and pan-cysteine cathepsin (JPM-OEt) inhibitors. We reasoned that, given stefin A is secreted from N1ME cells FIG. 7E), addition of inhibitors to the media was feasible. Indeed, we observed that CA-074 treatment rescued the phenotype caused by stefin A loss, reverting the invasive protrusions of the co-cultures back to the DCIS like state observed using WT N1ME cells (FIG. 8i, ii, quantified in 9v). JPM-OEt also reverted the invasive protrusions in the co-cultures, however not to the same extent as CA-074, and was not statistically significant across 3 experiments when compared to DMSO control (FIG. 8v). Use of the inhibitor alone (without the presence of the myoepithelial cells) did not inhibit invasion of the MDA-MB-231 cells (FIG. 8iii, iv, vi). This was also observed using recombinant stefin A (not shown). This suggests that the physical presence of myoepithelial cells and intact stefin A expression is required to block invasion, and that the substrate of cathepsin B is likely to be of myoepithelial origin.

Figure 10A:
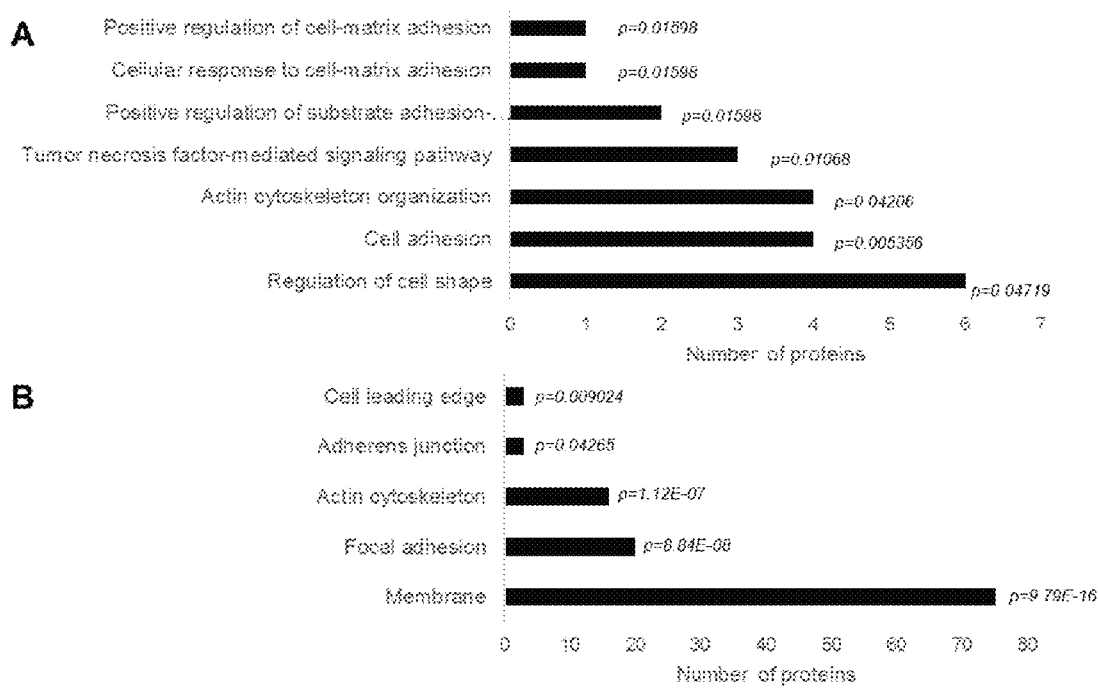
FIG. 10 Proteins identified by mass spectrometry associated with adhesion and cell attachment in myoepithelial cells. Gene ontologies (biological process and cellular compartment) significantly altered in N1ME wild type compared to stefin A low cell membrane preparations reflect enrichment of cell adhesion/attachment proteins. Data for each biological replicate was analyzed and related gene ontology and pathway networks (KEGG, DAVID) in proteins differentially expressed (normalized ratio spectral counts; Rsc±2) in N1ME wild type cells compared to N1ME stefin A low cells, with p-values indicated. The number of proteins differentially expressed associated with (A) biological processes and (B) cellular compartment is shown. (C) Volcano plot illustrates differentially abundant proteins relating to cell adhesion and attachment based on gene ontology classification. The −log 10 (Benjamini-Hochberg corrected P value) is plotted against the log 2 (fold change/Rsc: N1ME_low/N1ME). Proteins identified as more abundant (red) or less abundant (green) in the N1ME stefin A low cell membrane compared to N1ME wild type cell membrane. Proteins involved with desmosomes are identified with arrows. (D) DSG3 sequence profiles identified in trypsin-generated samples and summarized as normalized TIC intensity profiles between N1ME WT and N1ME stefin A heterozygote null cells (N1ME_low). DSG3 sequence distribution based on TIC and identified peptide sequence positions and protein domains (Extra, extracellular domain; Intra, intracellular domain; TM, transmembrane domain) are shown on the x axis. Normalized TIC relative to each peptide sequence is indicated on the y axis.
Figure 10B:
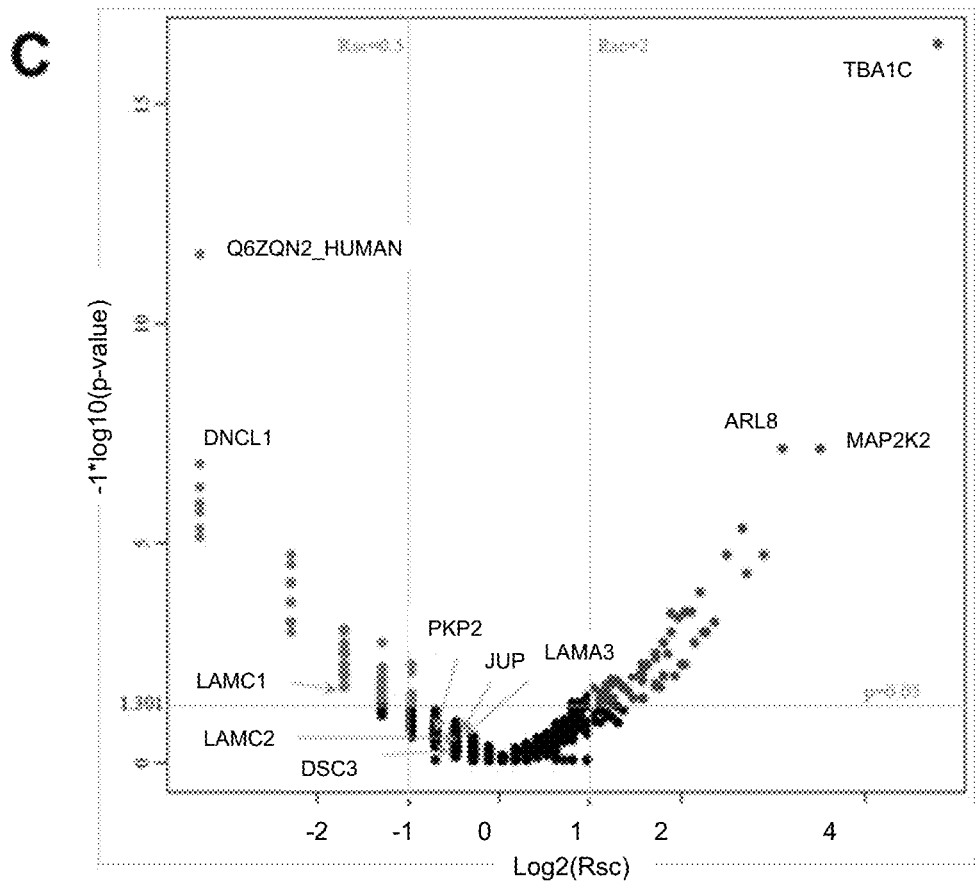
Figure 10B:
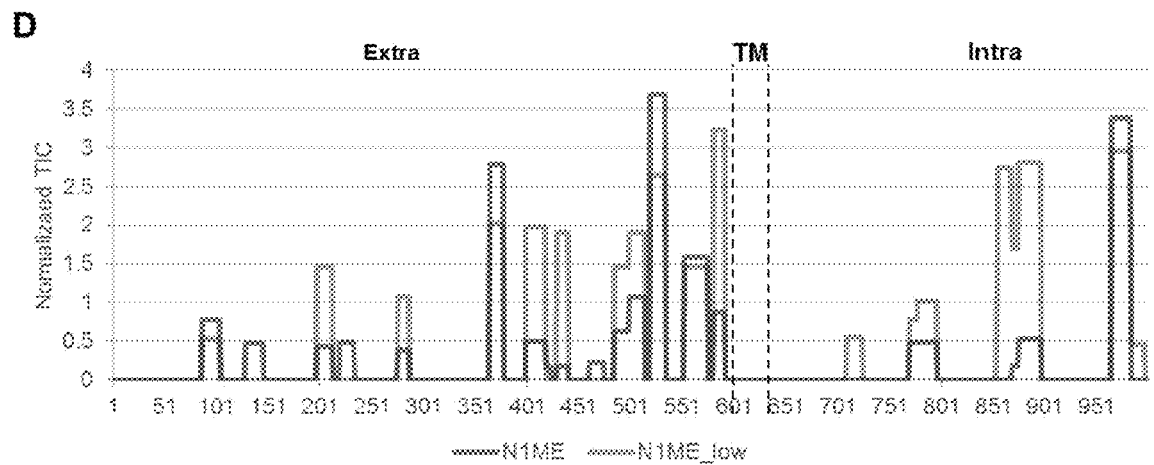

Changes in Adhesive Protein Profile and Decrease in Desmosomal Proteins at the Plasma Membrane of Stefin A Low N1ME Cells Our data above suggested that the function of myoepithelial stefin A in suppressing invasion relied on inhibiting the proteolytic activity of cathepsin B in myoepithelial cells. Given the known role of membrane and secreted cathepsin B in promoting invasion by cleaving membrane and extracellular proteins, membrane preparations of N1ME WT cells and N1ME stefin A low cells were compared by label-free quantitative mass spectrometry. For proteins differentially expressed (Rsc±2), gene ontology analysis (biological process and cellular compartment) revealed that N1ME stefin A low cells displayed a loss in expression of cell adhesive-associated proteins, specifically proteins interacting with or within desmosomes (FIG. 10A-C, Table 2). Together, this reflects the significant changes in the adhesive protein profile of the plasma cellular membrane associated with stefin A. Desmogleins (DSG) and desmocollins are the component of desmosomes that interact in the extracellular space, anchoring neighboring cells together. Mass spectrometry peptide analysis revealed changes to the abundance of intracellular: extracellular peptides for the myoepithelial specific desmoglein, DSG3 (Runswick, 2001). Intracellular peptides were more abundant in the membrane of the myoepithelial stefin A low cell line (FIG. 10D), suggesting enhanced cleavage in these cells.

Figure 9:
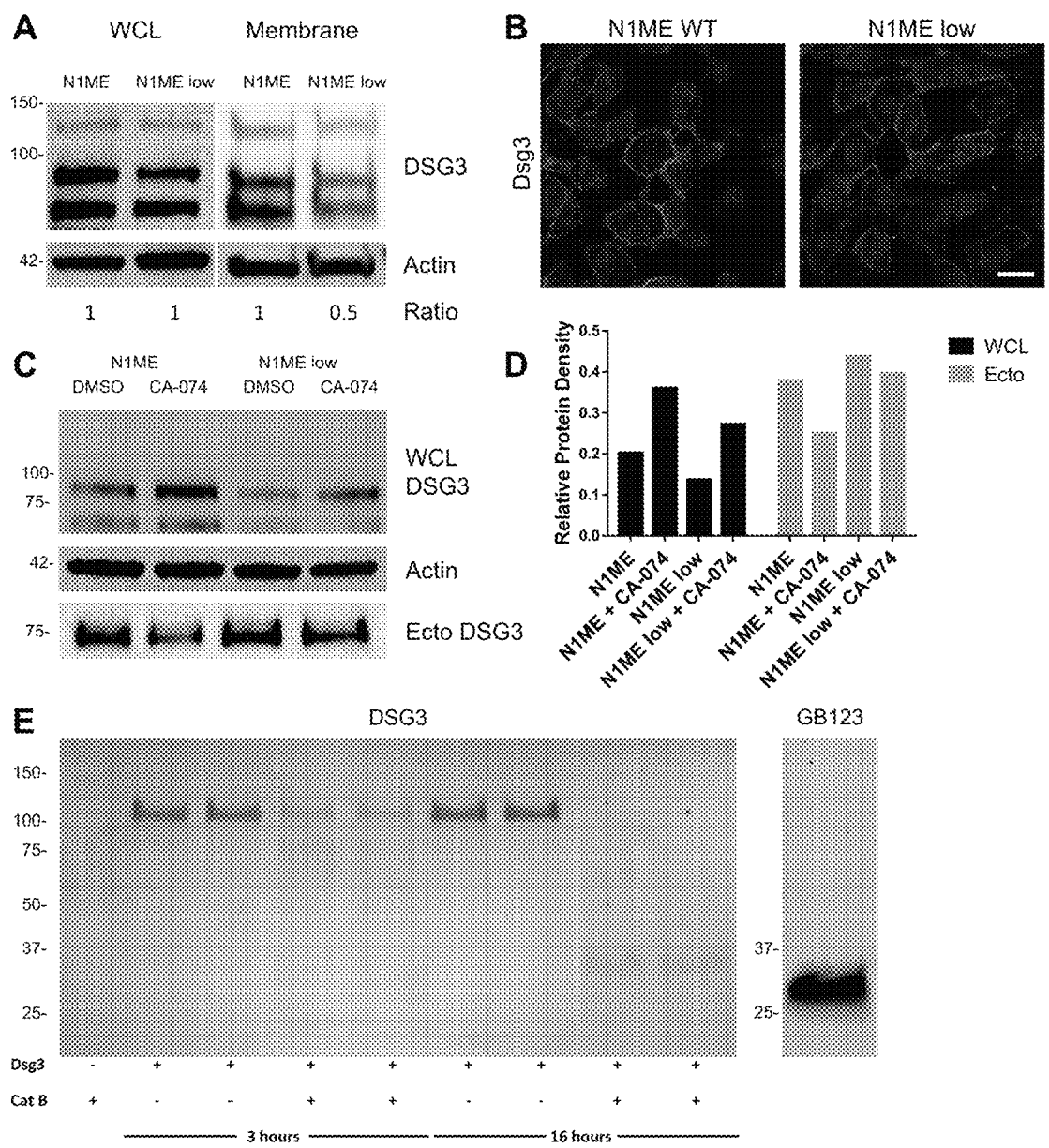
FIG. 9 Dysregulated plasma membrane adhesion protein network associated with loss of stefin A in myoepithelial cells. Characterization of Desmoglein-3 (DSG3) expression in N1ME stefin A wild type (N1ME) and N1ME stefin A low (N1ME low) cells. (A) DSG3 expected size 140 kDa, in WCL and membrane fraction. Densitometry analysis of DSG3 expression was performed using ImageJ, normalized to loading control (actin) and standardized to N1ME wild type protein level. Average shown as ratio, n=3. (B) N1ME stefin A wild type and low myoepithelial cells were stained with the primary antibody for DSG3 and the nuclei were stained with DAPI (blue). Primary antibody was detected by the use of a fluorescently conjugated secondary antibody. Negative controls had no staining (data not shown). Representative images of at least two independent experiments and multiple areas. Scale bar represents 20 μm. (C) Cells were treated with CA-074 (cathepsin B inhibitor) or DMSO (vehicle) for 72 hours and an increase in protein was noted for DSG3. During CA-074 or DMSO treatment, conditioned media was collected and ecto-DSG3 was identified at 75 kDa. Actin was used as loading control for all Western blots, expected band size of 42 kDa. (D) Densitometry for WCL and ecto-DSG3 protein compared to loading control (actin) in (C). (E) To determine if DSG3 can be cleaved by cathepsin B, recombinant protein with/without active recombinant cathepsin B were incubated at 37° C. for 3 or 16 hours, separated by gel electrophoresis and stained with Coomassie blue. Uncleaved DSG3 recombinant protein produces a band of approximately 105-110 kDa (expected). After incubation with cathepsin B, cleavage products are visible at approximately 75 and 30 kDa. Cathepsin B alone was included as control and the activity of cathepsin B was confirmed by the use of GB123 ABP.

Using Western blotting we validated DSG3 reduction in the membrane fraction of the N1ME stefin A low cells compared to WT cells (FIG. 9A). A reduction in membrane localization and/or enhanced cytoplasmic expression (arrow) was also observed by immunofluorescence (FIG. 9B). The reduction of DSG3 in the stefin A low cells was rescued in whole cell lysates by the addition of CA-074, suggesting that reduced DSG3 membrane expression in stefin A low cells was via the increased activity of cathepsin B (FIG. 9C and D). This was also observed upon analysis of the shed/cleaved proteins in the conditioned media. Cathepsin B inhibition decreased the cleaved extracellular domain of DSG3 (ecto-DSG3) from both N1ME wild type and stefin A low cells (FIG. 9C and D). Together, these data suggest that stefin A functions to inhibit cathepsin B cleavage of desmosomal proteins that would ultimately impact cell-cell adhesion.

TABLE 2

Proteins identified in plasma membrane fractions differentially expressed between N1ME wild type and N1ME stefin A low cells, involved in cell adhesion and cell attachment regulation.

| Gene Name | Protein Accession | | Protein Description | Plasma membrane (N1ME low v N1ME) | |
|---|---|---|---|---|---|
| | | | | Rsc (ratio) | p-val |
| MINK1 | Q8N4C8 | MINK1_HUMAN | Misshapen-like kinase 1 | −5.4 | 9.16E−05 |
| ASAP2 | O43150 | ASAP2_HUMAN | Arf-GAP with SH3 domain, ANK repeat and PH domain-containing protein 2 | −3.7 | 3.74E−03 |
| ZNF185 | O15231 | ZN185_HUMAN | Zinc finger protein 185 | −3.1 | 1.18E−02 |
| TJP2 | Q9UDY2 | ZO2_HUMAN | Tight junction protein ZO-2 | −3.1 | 1.18E−02 |
| SVIL | O95425 | SVIL_HUMAN | Supervillin | −2.9 | 1.01E−02 |
| MYH10 | P35580 | MYH10_HUMAN | Myosin-10 | −2.9 | 1.05E−03 |
| LAMC1 | P11047 | LAMC1_HUMAN | Laminin subunit gamma-1 | −2.5 | 3.93E−02 |

TABLE 2-continued

Proteins identified in plasma membrane fractions differentially expressed between N1ME wild type and N1ME stefin A low cells, involved in cell adhesion and cell attachment regulation.

| Gene Name | Protein Accession | | Protein Description | Plasma membrane (N1ME low v N1ME) | |
|---|---|---|---|---|---|
| | | | | Rsc (ratio) | p-val |
| TANC1 | Q9C0D5 | TANC1_HUMAN | Protein TANC1 | −2.4 | 3.93E−02 |
| ILKAP | Q9H0C8 | ILKAP_HUMAN | Integrin-linked kinase-associated serine/threonine phosphatase 2C | −2.4 | 7.30E−02 |
| FAM129B | Q96TA1 | NIBL1_HUMAN | Niban-flke protein 1 | −2.3 | 3.26E−02 |
| PALLD | Q8WX93 | PALLD_HUMAN | Palladin | −2.3 | 7.30E−02 |
| PTRF | Q6NZI2 | PTRF_HUMAN | Polymerase I and transcript release factor | −2.3 | 2.55E−02 |
| PDLIM5 | Q96HC4 | PDLI5_HUMAN | PDZ and LIM domain protein 5 | −2.3 | 2.57E−02 |
| TNS4 | Q8IZW8 | TENS4_HUMAN | Tensin-4 | −2.2 | 3.27E−02 |
| GAK | O14976 | GAK_HUMAN | Cyclin-G-associated kinase | −2.1 | 1.44E−01 |
| LANCL1 | O43813 | LANC1_HUMAN | LanC-like protein 1 | −2.1 | 1.37E−01 |
| MYH9 | P35579 | MYH9_HUMAN | Myosin-9 | −2.1 | 6.67E−03 |
| THBS1 | P07996 | TSP1_HUMAN | Thrombospondin-1 | −2.0 | 3.08E−02 |
| LRRC16A | Q5VZK9 | CARL1_HUMAN | F-actin-uncapping protein LRRC16A | −1.8 | 1.37E−01 |
| FER | P16591 | FER_HUMAN | Tyrosine-protein kinase Fer | −1.8 | 1.37E−01 |
| SYNE2 | Q8WXH0 | SYNE2_HUMAN | Nesprin-2 | −1.8 | #N/A |
| SYNE1 | Q8NF91 | SYNE1_HUMAN | Nesprin-1 | −1.8 | 1.37E−01 |
| ENAH | Q8N8S7 | ENAH_HUMAN | Protein enabled homolog | −1.7 | 1.97E−01 |
| PKP2 | Q99959 | PKP2_HUMAN | Plakophilin-2 | −1.7 | 2.12E−01 |
| SNTB2 | Q13425 | SNTB2_HUMAN | Beta-2-syntrophin | −1.6 | 4.73E−01 |
| PARVA | Q9NVD7 | PARVA_HUMAN | Alpha-parvin | −1.6 | 5.08E−01 |
| PRKD2 | Q9BZL6 | KPCD2_HUMAN | Serine/threonine-protein kinase D2 | −1.6 | 2.62E−01 |
| KDF1 | Q8NAX2 | KDF1_HUMAN | Keratinocyte differentiation factor 1 | −1.6 | 2.62E−01 |
| COL7A1 | Q02388 | CO7A1_HUMAN | Collagen alpha-1 | −1.6 | 4.54E−01 |
| CSK | P41240 | CSK_HUMAN | Tyrosine-protein kinase CSK | −1.5 | 3.89E−01 |
| ARPC2 | O15144 | ARPC2_HUMAN | Actin-related protein 2/3 complex subunit 2 | −1.5 | 4.25E−01 |
| SNAP23 | O00161 | SNP23_HUMAN | Synaptosomal-associated protein 23 | −1.5 | 5.07E−01 |
| JUP | P14923 | PLAK_HUMAN | Junction plakoglobin | −1.5 | 1.73E−01 |
| ARF1 | P84077 | ARF1_HUMAN | ADP-ribosylation factor 1 | −1.5 | 2.27E−01 |
| NPTN | Q9Y639 | NPTN_HUMAN | Neuroplastin | −1.5 | 3.75E−01 |
| MTDH | Q86UE4 | LYRIC_HUMAN | Protein LYRIC | −1.5 | 3.15E−01 |
| ACTN1 | P12814 | ACTN1_HUMAN | Alpha-actinin-1 | −1.5 | 1.61E−01 |
| CFL1 | P23528 | COF1_HUMAN | Cofilin-1 | −1.4 | 1.83E−01 |
| LAMA3 | Q16787 | LAMA3_HUMAN | Laminin subunit alpha-3 | −1.4 | 1.91E−01 |
| DSC3 | Q14574 | DSC3_HUMAN | Desmocollin-3 | −1.4 | 6.07E−01 |
| STOML2 | Q9UJZ1 | STML2_HUMAN | Stomatin-like protein 2, mitochondrial | −1.4 | 4.76E−01 |
| FSCN1 | Q16658 | FSCN1_HUMAN | Fascin | −1.4 | 2.18E−01 |
| AP2A1 | O95782 | AP2A1_HUMAN | AP-2 complex subunit alpha-1 | −1.4 | 3.15E−01 |
| ACTN4 | O43707 | ACTN4_HUMAN | Alpha-actinin-4 | −1.4 | 2.33E−01 |
| NDRG1 | Q92597 | NDRG1_HUMAN | Protein NDRG1 | −1.4 | 3.11E−01 |
| LAMC2 | Q13753 | LAMC2_HUMAN | Laminin subunit gamma-2 | −1.4 | 2.45E−01 |
| LIMA1 | Q9UHB6 | LIMA1_HUMAN | LIM domain and actin-binding protein 1 | −1.4 | 3.34E−01 |
| FERMT1 | Q9BQL6 | FERM1_HUMAN | Fermitin family homolog 1 | −1.3 | 3.26E−01 |
| PI4K2A | Q9BTU6 | P4K2A_HUMAN | Phosphatidylinositol 4-kinase type 2-alpha | −1.3 | 4.82E−01 |
| OCLN | Q16625 | OCLN_HUMAN | Occludin | 1.3 | 3.82E−01 |
| KRT1 | P04264 | K2C1_HUMAN | Keratin, type II cytoskeletal 1 | 1.4 | 2.86E−01 |
| RAP1A | P62834 | RAP1A_HUMAN | Ras-related protein Rap-1A | 1.4 | 2.53E−01 |
| FAP | Q12884 | SEPR_HUMAN | Prolyl endopeptidase FAP | 0.0 | 3.38E−01 |
| ARFGEF2 | Q9Y6D5 | BIG2_HUMAN | Brefeldin A-inhibited guanine nucleotide-exchange protein 2 | 1.5 | 3.15E−01 |
| FAM120A | Q9NZB2 | F120A_HUMAN | Constitutive coactivator of PPAR-gamma-like protein 1 | 1.5 | 3.88E−01 |
| CD44 | P16070 | CD44_HUMAN | CD44 antigen | 1.5 | 2.90E−01 |
| CIB1 | Q99828 | CIB1_HUMAN | Calcium and integrin-binding protein 1 | 1.6 | 2.62E−01 |
| COL12A1 | Q99715 | COCA1_HUMAN | Collagen alpha-1 | 1.9 | 3.15E−01 |
| DST | Q03001 | DYST_HUMAN | Dystonin | 1.6 | 1.75E−01 |
| ATP1B1 | P05026 | AT1B1_HUMAN | Sodium/potassium-transporting ATPase subunit beta-1 | 1.6 | 2.21E−01 |
| ATAD1 | Q8NBU5 | ATAD1_HUMAN | ATPase family AAA domain-containing protein 1 | 1.7 | 1.53E−01 |
| LAMB1 | P07942 | LAMB1_HUMAN | Laminin subunit beta-1 | 0.0 | 2.62E−01 |
| CDH4 | P55283 | CADH4_HUMAN | Cadherin-4 | 0.0 | 2.62E−01 |
| FAT2 | Q9NYQ8 | FAT2_HUMAN | Protocadherin Fat 2 | 1.7 | 2.62E−01 |
| PVR | P15151 | PVR_HUMAN | Poliovirus receptor | 1.8 | 1.73E−01 |
| CD109 | Q6YHK3 | CD109_HUMAN | CD109 antigen | 1.8 | 5.02E−02 |
| CDH13 | P55290 | CAD13_HUMAN | Cadherin-13 | 0.0 | 1.63E−01 |
| PKP4 | Q99569 | PKP4_HUMAN | Plakophilin-4 | 0.0 | 1.37E−01 |
| CD63 | P08962 | CD63_HUMAN | CD63 antigen | 1.2 | 1.37E−01 |
| PCDH1 | Q08174 | PCDH1_HUMAN | Protocadherin-1 | 1.9 | 1.37E−01 |
| GJA1 | P17302 | CXA1_HUMAN | Gap junction alpha-1 protein | 1.9 | 1.37E−01 |

TABLE 2-continued

Proteins identified in plasma membrane fractions differentially expressed between N1ME wild type and N1ME stefin A low cells, involved in cell adhesion and cell attachment regulation.

| Gene Name | Protein Accession | | Protein Description | Plasma membrane (N1ME low v N1ME) | |
|---|---|---|---|---|---|
| | | | | Rsc (ratio) | p-val |
| MPST | P25325 | THTM_HUMAN | 3-mercaptopyruvate sulfurtransferase | 2.1 | 7.30E−02 |
| PSEN1 | P49768 | PSN1_HUMAN | Presenilin-1 | 0.0 | 1.37E−01 |
| CLCA2 | Q9UQC9 | CLCA2_HUMAN | Calcium-activated chloride channel regulator 2 | 2.1 | 7.30E−02 |
| MELTF | P08582 | TRFM_HUMAN | Melanotransferrin | 2.1 | 7.30E−02 |
| SLC7A5 | Q01650 | LAT1_HUMAN | Large neutral amino acids transporter small subunit 1 | 2.2 | 1.88E−02 |
| FOCAD | Q5VW36 | FOCAD_HUMAN | Focadhesin | 2.2 | 8.17E−02 |
| MISP | Q8IVT2 | MISP_HUMAN | Mitotic interactor and substrate of PLK1 | 2.4 | 1.37E−01 |
| VEZT | Q9HBM0 | VEZA_HUMAN | Vezatin | 0.0 | 3.93E−02 |
| EPHB4 | P54760 | EPHB4_HUMAN | Ephrin type-B receptor 4 | 2.7 | 1.18E−02 |
| RUSC1 | Q9BVN2 | RUSC1_HUMAN | RUN arid SH3 domain-containing protein 1 | 3.3 | 2.14E−02 |
| RAB13 | P51153 | RAB13_HUMAN | Ras-related protein Rab-13 | 3.8 | 5.78E−04 |
| PPL | O60437 | PEPL_HUMAN | Periplakin | nc | nc |
| DNM2 | P50570 | DYN2_HUMAN | Dynamin-2 | nc | nc |
| NCKAP1 | Q9Y2A7 | NCKP1_HUMAN | Nck-associated protein 1 | nc | nc |
| IDE | P14735 | IDE_HUMAN | Insulin-degrading enzyme | nc | nc |
| C1QBP | Q07021 | C1QBP_HUMAN | Complement component 1 Q subcomponent-binding protein, mitochondrial | nc | nc |
| GOPC | Q9HD26 | GOPC_HUMAN | Golgi-associated PDZ and coiled-coil motif-containing protein | nc | nc |
| AIMP1 | Q12904 | AIMP1_HUMAN | Aminoacyl tRNA synthase complex-interacting multifunctional protein 1 | nc | nc |
| FN1 | P02751 | FINC_HUMAN | Fibronectin | nc | nc |
| MAPK14 | Q16539 | MK14_HUMAN | Mitogen-activated protein kinase 14 | nc | nc |
| MEMO1 | Q9Y316 | MEMO1_HUMAN | Protein MEMO1 | nc | nc |
| PRKAR1A | P10644 | KAP0_HUMAN | cAMP-dependent protein kinase type I-alpha regulatory subunit | nc | nc |
| CASP3 | P42574 | CASP3_HUMAN | Caspase-3 | nc | nc |
| ESYT1 | Q9BSJ8 | ESYT1_HUMAN | Extended synaptotagmin-1 | nc | nc |
| VDAC1 | P21796 | VDAC1_HUMAN | Voltage-dependent anion-selective channel protein 1 | nc | nc |
| BCAR1 | P56945 | BCAR1_HUMAN | Breast cancer anti-estrogen resistance protein 1 | nc | nc |
| LAMP1 | P11279 | LAMP1_HUMAN | Lysosome-associated membrane glycoprotein 1 | nc | nc |
| GNAI2 | P04899 | GNAI2_HUMAN | Guanine nucleotide-binding protein G | nc | nc |
| CTNNB1 | P35222 | CTNB1_HUMAN | Catenin beta-1 | nc | nc |
| DLG1 | Q12959 | DLG1_HUMAN | Disks large homolog 1 | nc | nc |
| DNAJC9 | Q8WXX5 | DNJC9_HUMAN | DnaJ homolog subfamily C member 9 | nc | nc |
| SYMPK | Q92797 | SYMPK_HUMAN | Symplekin | nc | nc |
| CTNNA1 | P35221 | CTNA1_HUMAN | Catenin alpha-1 | nc | nc |
| RIC8A | Q9NPQ8 | RIC8A_HUMAN | Synembryn-A | nc | nc |
| TLN1 | Q9Y490 | TLN1_HUMAN | Talin-1 | nc | nc |
| GOT2 | P00505 | AATM_HUMAN | Aspartate aminotransferase, mitochondrial | nc | nc |
| PPP5C | P53041 | PPP5_HUMAN | Serine/threonine-protein phosphatase 5 | nc | nc |
| TRIP10 | Q15642 | CIP4_HUMAN | Cdc42-interacting protein 4 | nc | nc |
| MPDZ | O75970 | MPDZ_HUMAN | Multiple PDZ domain protein | nc | nc |
| PACSIN3 | Q9UKS6 | PACN3_HUMAN | Protein kinase C and casein kinase substrate in neurons protein 3 | nc | nc |
| SH3KBP1 | Q96B97 | SH3K1_HUMAN | SH3 domain-containing kinase-binding protein 1 | nc | nc |
| PRKACA | P17612 | KAPCA_HUMAN | cAMP-dependent protein kinase catalytic subunit alpha | nc | nc |
| TRPV1 | Q8NER1 | TRPV1_HUMAN | Transient receptor potential cation channel subfamily V member 1 | nc | nc |
| RDX | P35241 | RADI_HUMAN | Radixin | nc | nc |
| TJP1 | Q07157 | ZO1_HUMAN | Tight junction protein ZO-1 | nc | nc |
| CRK | P46108 | CRK_HUMAN | Adapter molecule crk | nc | nc |
| FLNB | O75369 | FLNB_HUMAN | Filamin-B | nc | nc |
| ITGA6 | P23229 | ITA6_HUMAN | Integrin alpha-6 | nc | nc |
| RAB14 | P61106 | RAB14_HUMAN | Ras-related protein Rab-14 | nc | nc |
| ABI1 | Q8IZP0 | ABI1_HUMAN | Abl interactor 1 | nc | nc |
| CKAP4 | Q07065 | CKAP4_HUMAN | Cytoskeleton-associated protein 4 | nc | nc |
| ADI1 | Q9BV57 | MTND_HUMAN | 1,2-dihydroxy-3-keto-5-methylthiopentene dioxygenase | nc | nc |
| S100A9 | P06702 | S10A9_HUMAN | Protein S100-A9 | nc | nc |
| ITGAV | P06756 | ITAV_HUMAN | Integrin alpha-V | nc | nc |

TABLE 2-continued

Proteins identified in plasma membrane fractions differentially expressed between N1ME wild type and N1ME stefin A low cells, involved in cell adhesion and cell attachment regulation.

| Gene Name | Protein Accession | | Protein Description | Plasma membrane (N1ME low v N1ME) | |
|---|---|---|---|---|---|
| | | | | Rsc (ratio) | p-val |
| PKP1 | Q13835 | PKP1_HUMAN | Plakophilin-1 | nc | nc |
| ITGB1 | P05556 | ITB1_HUMAN | Integrin beta-1 | nc | nc |
| SRC | P12931 | SRC_HUMAN | Proto-oncogene tyrosine-protein kinase Src | nc | nc |
| ITGA3 | P26006 | ITA3_HUMAN | Integrin alpha-3 | nc | nc |
| FLRT3 | Q9NZU0 | FLRT3_HUMAN | Leucine-rich repeat transmembrane protein FLRT3 | nc | nc |
| ITGB6 | P18564 | ITB6_HUMAN | Integrin beta-6 | nc | nc |
| LAMP2 | P13473 | LAMP2_HUMAN | Lysosome-associated membrane glycoprotein 2 | nc | nc |
| ITGA2 | P17301 | ITA2_HUMAN | Integrin alpha-2 | nc | nc |
| APP | P05067 | A4_HUMAN | Amyloid beta A4 protein | nc | nc |
| LPXN | O60711 | LPXN_HUMAN | Leupaxin | nc | nc |
| PNN | Q9H307 | PININ_HUMAN | Pinin | nc | nc |
| TMED10 | P49755 | TMEDA_HUMAN | Transmembrane emp24 domain-containing protein 10 | nc | nc |
| EGFR | P00533 | EGFR_HUMAN | Epidermal growth factor receptor | nc | nc |
| AAK1 | Q2M2I8 | AAK1_HUMAN | AP2-associated protein kinase 1 | nc | nc |
| FBLIM1 | Q8WUP2 | FBLI1_HUMAN | Filamin-binding LIM protein 1 | nc | nc |
| CORO1C | Q9ULV4 | COR1C_HUMAN | Coronin-1C | nc | nc |
| CAPN2 | P17655 | CAN2_HUMAN | Calpain-2 catalytic subunit | nc | nc |
| DSG3 | P32926 | DSG3_HUMAN | Desmoglein-3 | nc | nc |
| DOCK5 | Q9H7D0 | DOCK5_HUMAN | Dedicator of cytokinesis protein 5 | nc | nc |

Gene Name, Protein accession, protein description derived from UniProt protein database, Rsc (normalized ratio spectral counts) For each protein the Fisher's exact test was applied to significant assigned spectra, with resulting p-values corrected for multiple testing using the Benjamini-Hochberg procedure (1) and statistics performed as previously described (2). For gene ontology analyses, UniProt was utilized, while for pathway analyses, KEGG (Kanehisa and Goto, 2000) and DAVID (Huang et al., 2009) resources were utilized.

To confirm that DSG3 is in fact a direct cathepsin B substrate, recombinant DSG3 was incubated with active cathepsin B in vitro. Visualization on an SDS-PAGE gel confirmed cleavage by cathepsin B (FIG. 9E). A previously reported substrate of cathepsin B is E-cadherin (Gocheva, 2006). However, in our studies there were minimal differences in E-cadherin between N1ME wild type and stefin A low cells, and CA-074 treatment of myoepithelial cells did not affect E-cadherin expression in whole cell lysates or ecto-protein (FIG. 11A and B).

Figure 11:
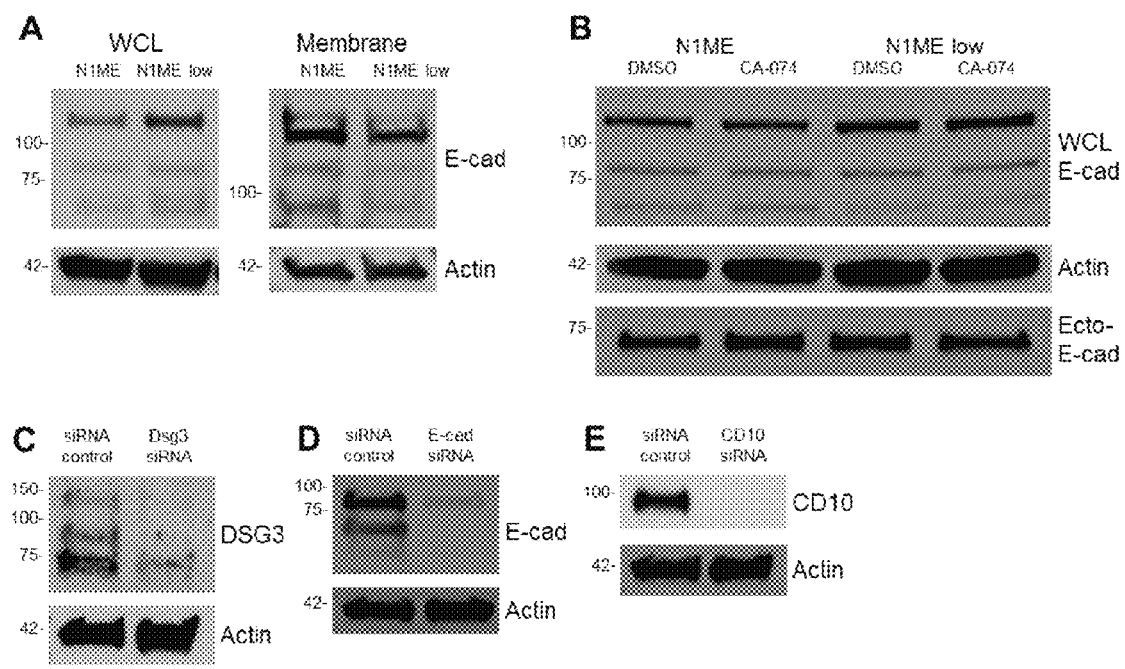
FIG. 11 Western blots of cell adhesion proteins. (A) Western blots of E-cadherin in whole cell lysates (WCL) or membrane preparations from N1ME wild type and N1ME stefin A low cells, expected band size of 135 kDa. (B) N1ME stefin A wild type or stefin A low cells were treated with CA-074 for 72 hours, then cells and supernatant were collected for analysis of WCL and ecto-E-cadherin, respectively. Confirmation of siRNA knockdown of adhesion proteins in N1ME myoepithelial cell line as shown by immunoblotting, compared to siRNA non-targeting control. (C) Desmoglein 3, expected band size of 140 kDa. (D) E-cadherin (E-cad), expected band size of 135 kDa. (E) CD10, expected band size of 85 kDa. Actin was used as loading control for all western blots, expected band size of 42 kDa.
Figure 12:
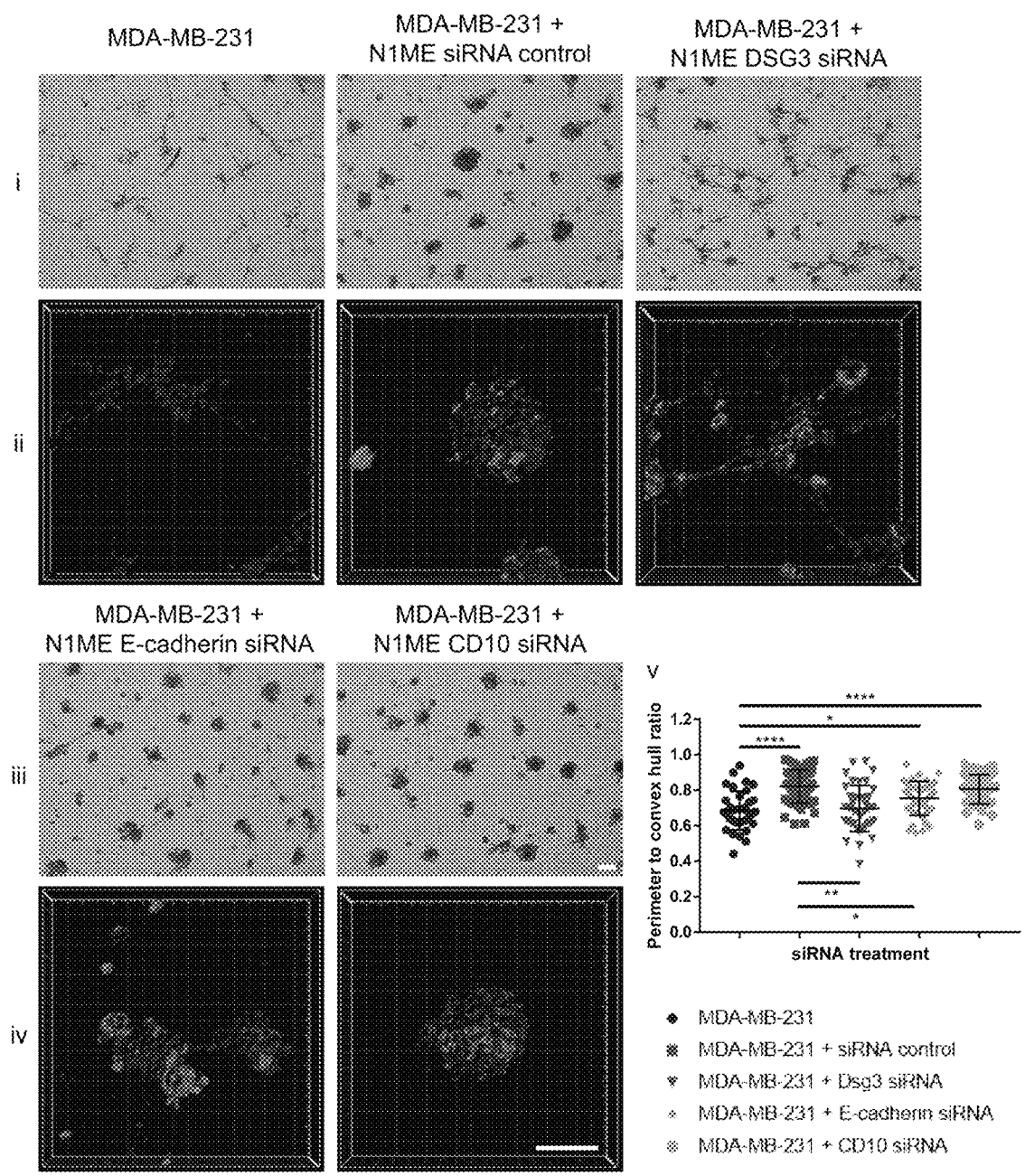
FIG. 12 Knockdown of adhesion proteins in myoepithelial cells inhibits reversion of invasiveness of MDA-MB-231 in 3D co-culture. MDA-MB-231 cells cultured alone or co-cultured with N1ME cells transfected with siRNA for DSG3, E-cadherin, CD10 or non-targeting control. (i, iii) Bright field images of MDA-MB-231 (not labelled) co-cultured with myoepithelial cells. (ii, iv) Confocal images, rendered in Imaris, of MDA-MB-231 Hoechst stained (blue) alone or co-cultured with myoepithelial cells (red). Scale bar represents 200 μm. (v) Quantification of invasive outgrowths as described in FIG. 6. DSG3 siRNA was not significantly different in comparison to MDA-MB-231. CD10 siRNA was not significantly different to siRNA control. *p<0.05, p<0.01, **p<0.0001. n=2.

To confirm the effect of decreased adhesion proteins in myoepithelial cells, knockdown of DSG3, E-cadherin and CD10 (a non-adhesion myoepithelial protein that served as a control) was performed by siRNA and confirmed by Western blot (FIG. 11C-E). The cells were seeded into 3D co-cultures with MDA-MB-231 cells (FIG. 12). Knockdown of DSG3 in the myoepithelial cells resulted in a phenotype similar to that seen with the stefin A low cell line (FIG. 6), and invasion was comparable to MDA-MB-231 cells cultured alone (FIG. 12v). Knockdown of E-cadherin had an intermediate phenotype and CD10 did not impact the suppressive function of myoepithelial cells, as expected (FIG. 12iii and iv). These results demonstrate that loss of adhesion proteins blocks myoepithelial suppressive function and allows for cancer cell invasion in a 3D model.

Treatment with Cathepsin B Inhibitors Decreases Invasive Growth In Vivo

Figure 13:
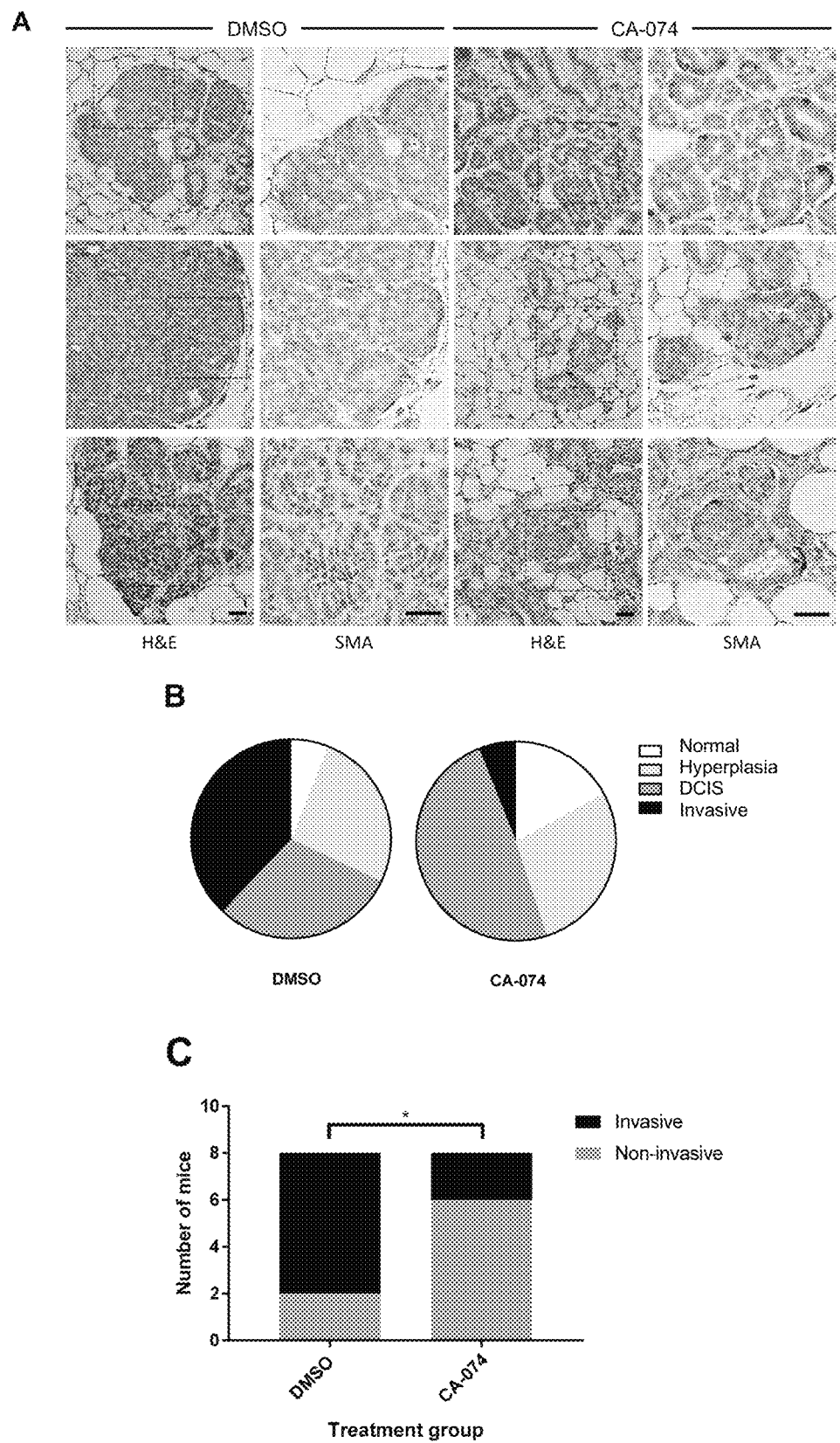
FIG. 13 Cysteine cathepsin inhibition in vivo decreases development of invasive lesions in mouse mammary glands. (A) Representative images of second, third or fourth mammary glands with DCIS/invasive regions from mice treated with 50 mg/kg CA-074 or DMSO (control) in saline for 20 days. At day 50, mice were culled and mammary glands harvested, sectioned, and stained by H&E. Serial sections were stained with anti-smooth muscle actin (myoepithelial marker) and visualized with DAB. These sections were counterstained with hematoxylin. Representative images from eight mice per group. Scale bars represent 25 μm. Mammary glands of all mice were blindly scored by a pathologist and were determined to be invasive or non-invasive (normal, hyperplasia, DCIS). (B) Percentage of mammary gland with each diagnosis per group were graphed. (C) The final diagnosis for each mouse was determined and compared between groups. *p<0.05 by Chi-square test.

Our results using the 3D DCIS model suggest that cysteine cathepsin inhibitors have important roles in the DCIS-to-invasive transition. To test the therapeutic efficacy of cathepsin inhibitors in an in vivo model of early tumorigenesis, we treated MMTV-PyMT mice (which spontaneously develop mammary gland tumors) with the cathepsin B-selective inhibitor CA-074 for the time period between DCIS development and development of IDC (30-50 days). At the time of treatment cessation, mammary glands were histologically evaluated, including assessment of smooth muscle actin expression, as a myoepithelial marker (FIG. 13A). Comparison of the treatment (CA-074) versus control (DMSO) groups revealed that cathepsin B inhibition decreased the number of invasive regions throughout the mammary gland (FIG. 13B). CA-074-treated mice developed DCIS yet rarely progressed to IDC at experimental endpoint (2/8), in contrast to the development of invasive disease in most of the control group (6/8) (FIG. 13C). These results support our in vitro observations that cysteine cathepsin inhibitors suppress early invasion events.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Example 2

Recurrence of Invasive Cancer

Samples were surgically resected from pre-invasive lesions (DCIS) from 3 patients in 1997, 2004 and 2001 respectively (Identified as Patient 1997, Patient 2004 and Patient 2001) and the samples were archived. These patients were subsequently followed up clinically over 10 years.

Figure 14:
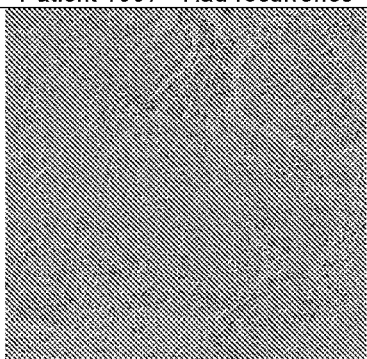
FIG. 14 Stefin A expression in archived DCIS tissue of patients where over 10 year follow-up was available to determine those that went on to develop invasive disease. Sections of formalin-fixed, paraffin-embedded tissue, retrieved at time of initial surgery, were stained with rabbit anti-human stefin A and visualized with DAB (brown). All sections were counterstained with hematoxylin (blue nuclei). Patient 1997, no myoepithelial stefin A expression evident in the pre-invasive lesion, later developed recurrent breast cancer. Patient 2004, no myoepithelial stefin A expression evident, later presented with recurrent breast cancer. Patient 2001, positive myoepithelial and epithelial stefin A expression evident, has not had a recurrence of breast cancer (to date).
Figure 14:
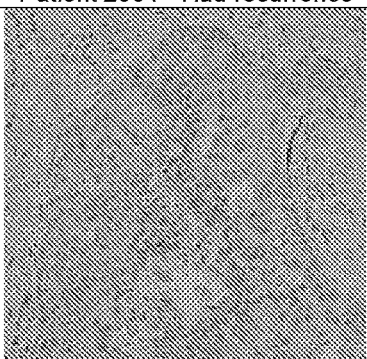
Figure 14:
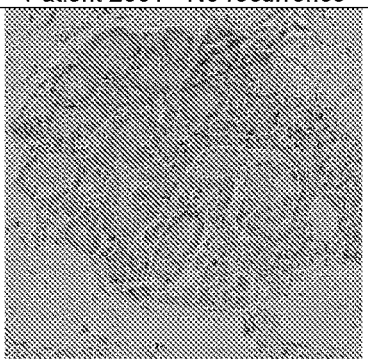

The archived samples of Patient 1997, Patient 2004 and Patient 2001 were subsequently analysed for Stefin A (FIG. 14). Staining of Stefin A was carried out as previously described (Immunohistochemistry (IHC)). Patient 1997 and 2004 showed low to no staining of Stefin A and later developed a clinically diagnosed invasive neoplastic lesion, confirmed by methods such as mammogram and core biopsy.

In contrast, the archived sample of Patient 2001 displays normal levels of Stefin A. Patient 2001 has had annual follow up for approximately 10 years and has no recurrence of breast cancer.

BIBLIOGRAPHY

Alon et al. (1999) Proc. Natl. Acad. Sci. USA: 96, 6745-6750
Barsky et al. (2005) J Mammary Gland Biol Neoplasia., 10(3):249-60.
Blum et al. (2007) Nat Chem Biol., 3(10):668-77.
Brosch et al. (2009) Journal of proteome research. 8(6): 3176-81.
Chang et al. (2010) Proteomics., 10(14):2644-60.
DeRisi, et al. (1996) Nature Genetics 14:457-460
Dubin et al. (2005) Cell Mol Life Sci., 62(6):653-69.
Erlich, (1989) J Clin Immunol 9(6):437-47
Fujiki et al. (1982) J Cell Biol. 93(1):97-102.
Germer et al. (2000) Genome Res. 10:258-266
Gocheva et al. (2006) Genes & Development., 20(5):543-56.
Gopal et al. (2015) Oncotarget. 6(15):13718-30.
Greening et al. (2013) Biochim Biophys Acta. 1834(11): 2396-407.
Greening et al. (2016) Biology of reproduction. 94(2):38.
Gudjonsson et al. (2002) J Cell Sci., 115(Pt 1):39-50.
Guo et al., (1994) Nucleic Acids Res. 22:5456-5465.
Heid et al., (1996) Genome Res. 6:986-994.
Huang et al. (2009) Nature Protoc. 4(1): 44-57.
Kanehisa and Goto (2000) Nucleic Acids Res. 28: 27-30.
Keller et al., (2002) Analytical chemistry. 74(20):5383-92.
Keppler et al. (2006) Cancer Lett., 235(2):159-76.
Maskos and Southern (1992) Nuc. Acids Res. 20:1679-84
Miller et al. (2000) Journal of the National Cancer Institute., 92(14):1185-6.
Moore et al. (1988) BBA, 1402:239-249
Mullins et al. (2012) Biological chemistry., 393(12):1405-16.
Mullis et al., (1987) Methods Enzymol 155:335-50
Nesvizhskii et al. (2005) Mol Cell Proteomics. 4(10):1419-40.
Parker B S, et al. (2008) Journal of Pathology 214(3):337-46
Pease et al. (1994) Proc. Natl. Acad. Sci. USA 91(11):5022-5026
Polyak (2005) J Mammary Gland Biol Neoplasia., 10(3): 231-47.
Runswick et al. (2001) Nat Cell Biol., 3(9):823-30.
Schena, et al. (1995) Science 270:467-470
Schindelin et al. (2012) Nature methods., 9(7):676-82.
Smith et al. (1992) Science 258:1122-1126
Sternlicht et al. (1997) Med Hypotheses., 48(1):37-46.
Sternlicht et al. (1997a) Clinical Cancer Research., 3(11): 1949-58.
Strojan et al. (2004) Br J Cancer. 2004; 90(10):1961-8.
Strojnik et al. (2000) Pflugers Arch., 439(3 Suppl):R122-3.
Tang et al. (2015) BioMed Research International.; 2015: 617143.
Tang et al. (2016) The R Journal; 8.
Urdea et al. (1991) Nucleic Acids Symp. Ser., 24:197-200
Verdoes et al. (2013) Journal of the American Chemical Society., 135(39):14726-30.
Vichai, et al. (2006). Nat Protocols 1, 1112-1116.
Wedemeyer et al. (2002) Clinical Chemistry 48:9 1398-1405
Weissleder et al. (2000) Nature Medicine 6:351-355
Wickham (2009) ggplot2: Elegant Graphics for Data Analysis. 1 ed. New York: Springer-Verlag;
Wood et al. (2014) Oncology (Williston Park, NY); 28 Suppl 2:C2, 1-8, C3.
Zardawi et al. (2010) Histopathology., 56(3):286-96.
U.S. Pat. No. 4,683,195
U.S. Pat. No. 6,410,229
U.S. Pat. No. 5,573,909
U.S. Pat. No. 5,326,692
U.S. Pat. No. 5,227,487
U.S. Pat. No. 5,274,113
U.S. Pat. No. 5,405,975
U.S. Pat. No. 5,433,896
U.S. Pat. No. 5,442,045
U.S. Pat. No. 5,451,663
U.S. Pat. No. 5,453,517
U.S. Pat. No. 5,459,276
U.S. Pat. No. 5,516,864
U.S. Pat. No. 5,648,270
U.S. Pat. No. 5,723,218
WO 93/06121

The invention claimed is:

1. A method of determining whether to provide a therapy to a mammal presenting with pre-invasive breast neoplasia, said method comprising determining the level of expression of Stefin A in breast myoepithelial cells from said mammal, wherein said breast myoepithelial cells are present in the same tissue region as the pre-invasive breast neoplasia or present adjacent or proximal to the pre-invasive breast neoplasia, wherein:
   (i) a decrease in the level of Stefin A expression relative to a control level is indicative of a need for a therapy for breast neoplasia, wherein said decrease in the level of Stefin A relative to a control level is indicative of a progression in the transition of the pre-invasive breast neoplasia to an invasive breast neoplasia; or
   (ii) no change or increase in the level of Stefin A expression relative to a control level is indicative of no need for a therapy for breast neoplasia,
   further comprising providing one or more of the following to said mammals identified as having a need for a therapy:
   a) Cysteine cathepsin inhibitors;
   b) Surgical excision;
   c) Radiotherapy;
   d) Chemotherapy; or
   e) Targeted antibody therapy.

2. The method according to claim 1, wherein said pre-invasive breast neoplasia is breast carcinoma.

3. The method according to claim 1, wherein said pre-invasive breast neoplasia is breast lobular or ductal neoplasia.

4. The method according to claim 1, wherein said pre-invasive breast neoplasia is ductal carcinoma in situ (DCIS).

5. The method according to claim 1, wherein the level of expression of Stefin A is determined by detecting RNA transcripts, cDNA transcribed from the RNA transcripts or a protein expression product from the RNA transcripts.

6. The method according to claim 1, wherein the level of expression of Stefin A in myoepithelial cells is determined by detecting cathepsin B protease activity, wherein increased cathepsin B protease activity relative to a control level is indicative of a decrease in the level of Stefin A expression and the need for a therapy for said breast neoplasia.

7. The method according to claim 1, wherein said method further comprises detecting a change in expression of one or more of the following membrane adhesion molecules:
   a. Desmoglein-3 (DSG3); or
   b. Misshapen-like kinase 1 (MINK1), Arf-GAP with SH3 domain, ANK repeat and PH domain-containing protein 2 (ASAP2), Zinc finger protein 185 (ZNF185), Tight junction protein ZO-2 (TJP2), Supervillin (SVIL), Myosin-10 (MYH10), Laminin subunit gamma-1 (LAMC1), Protein TANC1 (TANC1), Integrin-linked kinase-associated serine/threonine phosphatase 2C (ILKAP), Niban-like protein 1 (FAM129B), Palladin (PALLD), Polymerase I and transcript release factor (PTRF), PDZ and LIM domain protein 5 (PDLIM5), Tensin-4 (TNS4), Cyclin-G-associated kinase (GAK), LanC-like protein 1 (LANCL1), Myosin-9 (MYH9), Thrombospondin-1 (THB S1), F-actin-uncapping protein LRRC16A (LRRC16A), Tyrosine-protein kinase Fer (FER), Nesprin-2 (SYNE2), Nesprin-1 (SYNE1), Protein enabled homolog (ENAH), Plakophilin-2 (PKP2), Beta-2-syntrophin (SNTB2), Alpha-parvin (PARVA), Serine/threonine-protein kinase D2 (PRKD2), Keratinocyte differentiation factor 1 (KDF1), Collagen alpha-1 (COL7A1), Tyrosine-protein kinase CSK (CSK), Actin-related protein 2/3 complex subunit 2 (ARPC2), Synaptosomal-associated protein 23 (SNAP23), Junction plakoglobin (JUP), ADP-ribosylation factor 1 (ARF1), Neuroplastin (NPTN), Protein LYRIC (MTDH), Alpha-actinin-1 (ACTN1), Cofilin-1 (CFL1), Laminin subunit alpha-3 (LAMA3), Desmocollin-3 (DSC3), Stomatin-like protein 2, mitochondrial (STOML2), Fascin (FSCN1), AP-2 complex subunit alpha-1 (AP2A1), Alpha-actinin-4 (ACTN4), Protein NDRG1 (NDRG1), Laminin subunit gamma-2 (LAMC2), LIM domain and actin-binding protein 1 (LIMA1), Fermitin family homolog 1 (FERMT1), Phosphatidylinositol 4-kinase type 2-alpha (PI4K2A), Occludin (OCLN), Keratin, type II cytoskeletal 1 (KRT1), Ras-related protein Rap-1A (RAP1A), Prolyl endopeptidase FAP (FAP), Brefeldin A-inhibited guanine nucleotide-exchange protein 2 (ARFGEF2), Constitutive coactivator of PPAR-gamma-like protein 1 (FAM120A), CD44 antigen (CD44), Calcium and integrin-binding protein 1 (CIB1), Collagen alpha-1 (COL12A1), Dystonin (DST), Sodium/potassium-transporting ATPase subunit beta-1 (ATP1B1), ATPase family AAA domain-containing protein 1 (ATAD1), Laminin subunit beta-1 (LAMB1), Cadherin-4 (CDH4), Protocadherin Fat 2 (FAT2), Poliovirus receptor (PVR), CD109 antigen (CD109), Cadherin-13 (CDH13), Plakophilin-4 (PKP4), CD63 antigen (CD63), Protocadherin-1 (PCDH1), Gap junction alpha-1 protein (GJA1), 3-mercaptopyruvate sulfurtransferase (MPST), Presenilin-1 (PSEN1), Calcium-activated chloride channel regulator 2 (CLCA2), Melanotransferrin (MELTF), Large neutral amino acids transporter small subunit 1 (SLC7A5), Focadhesin (FOCAD), Mitotic interactor and substrate of PLK1 (MISP), Vezatin (VEZT), Ephrin type-B receptor 4 (EPHB4), RUN and SH3 domain-containing protein 1 (RUSC1), or Ras-related protein Rab-13 (RAB13).

8. The method according to claim 1, wherein said method further comprises determining the presence or amount of estrogen receptor, progesterone receptor or human epidermal growth factor receptor 2 (HER2) on said myoepithelial cells.

9. The method according to claim 1, wherein the mammal is a human.

10. The method of claim 1, wherein said control level is a level of expression of Stefin A found in healthy breast myoepithelial cells.

11. The method of claim 1, wherein said control level is a level of expression of Stefin A from a previous analysis of said mammal.

12. The method of claim 1, wherein said pre-invasive breast neoplasia is hyperplasia.

13. A method for the treatment of pre-invasive breast neoplasia, the method comprising:
   a. obtaining a biological sample comprising breast myoepithelial cells from a subject presenting with a pre-invasive breast neoplasia, wherein the breast myoepithelial cells are from the same tissue region as the breast neoplasia or adjacent or proximal to the pre-invasive breast neoplasia;
   b. screening the breast myoepithelial cells in the biological sample for altered Stefin A expression relative to a control level, wherein:
      i. decreased Stefin A expression in the breast myoepithelial cells relative to the control level is indicative of a progression in the transition of the pre-invasive breast neoplasia to an invasive breast neoplasia and a need for therapy for breast neoplasia; and
      ii. no change or increased Stefin A expression in the breast myoepithelial cells relative to the control level indicates that the subject does not require therapy; and
   c. based on the assessment in step ( ), treating a subject identified as having a need for therapy with one or more or all of cysteine cathepsin inhibitor therapy, surgical excision, radiotherapy, chemotherapy and targeted antibody therapy.

14. The method of claim 13, wherein the myoepithelial Stefin A expression is mRNA, cDNA or protein expression.

* * * * *